US006866037B1

(12) United States Patent
Aslin et al.

(10) Patent No.: US 6,866,037 B1
(45) Date of Patent: Mar. 15, 2005

(54) INHALER

(75) Inventors: Goran Aslin, Njurunda (SE); Oscar Alexandersson, Arsta (SE); Nils Blomqvist, deceased, late of Bro (SE); by Rigmor Blomqvist, legal representative, Bro (SE); Lennart Brunnberg, Tyreso (SE)

(73) Assignee: SHL Medical AB, Nacka (SE)

( * ) Notice: Subject to any disclaimer, the term of this patent is extended or adjusted under 35 U.S.C. 154(b) by 0 days.

(21) Appl. No.: 10/018,242
(22) PCT Filed: Jun. 16, 2000
(86) PCT No.: PCT/SE00/01278

§ 371 (c)(1),
(2), (4) Date: Oct. 1, 2002

(87) PCT Pub. No.: WO00/78378

PCT Pub. Date: Dec. 28, 2000

(30) Foreign Application Priority Data

| Jun. 18, 1999 | (SE) | 9902349 |
| Jun. 21, 1999 | (SE) | 9902365 |
| Oct. 12, 1999 | (SE) | 9903663 |
| Oct. 12, 1999 | (SE) | 9903678 |
| Mar. 6, 2000 | (SE) | 0000732 |
| Mar. 6, 2000 | (SE) | 0000733 |

(51) Int. Cl.[7] ............................. A61M 11/00
(52) U.S. Cl. ............ 128/200.23; 128/200.12; 128/203.23
(58) Field of Search ............. 128/200.12, 200.14, 128/200.23, 203.12, 203.15, 203.23

(56) References Cited

U.S. PATENT DOCUMENTS

| 3,151,618 A | * | 10/1964 | Wakeman | 128/200.23 |
| 3,456,644 A | * | 7/1969 | Thiel | 128/200.23 |
| 5,027,808 A | * | 7/1991 | Rich et al. | 128/203.23 |
| 5,069,204 A | * | 12/1991 | Smith et al. | 128/200.23 |
| 5,119,806 A | * | 6/1992 | Palson et al. | 128/200.14 |
| 5,347,998 A | * | 9/1994 | Hodson et al. | 128/200.23 |
| 5,447,150 A | * | 9/1995 | Bacon | 128/200.14 |
| 5,826,571 A | * | 10/1998 | Casper et al. | 128/200.23 |

* cited by examiner

*Primary Examiner*—Henry Bennett
*Assistant Examiner*—Andrea M. Ragonese
(74) *Attorney, Agent, or Firm*—Young & Thompson

(57) ABSTRACT

Device for use with an inhaler, the inhaler having a body, an aerosol canister arranged in the body containing medicament, including a metered dose chamber and able to dispense a metered dose of the medicament, a nozzle in fluid communication with the canister, an opening for dispensing of the medicament in fluid communication with the nozzle. The device includes elements for activating the canister to open and dispense the medicament in response to an airflow in the inhaler caused by inhalation of a user through the opening, return elements for deactivating the canister to close it, characterized in that the return elements deactivate the canister when the airflow drops below a certain threshold value.

12 Claims, 24 Drawing Sheets

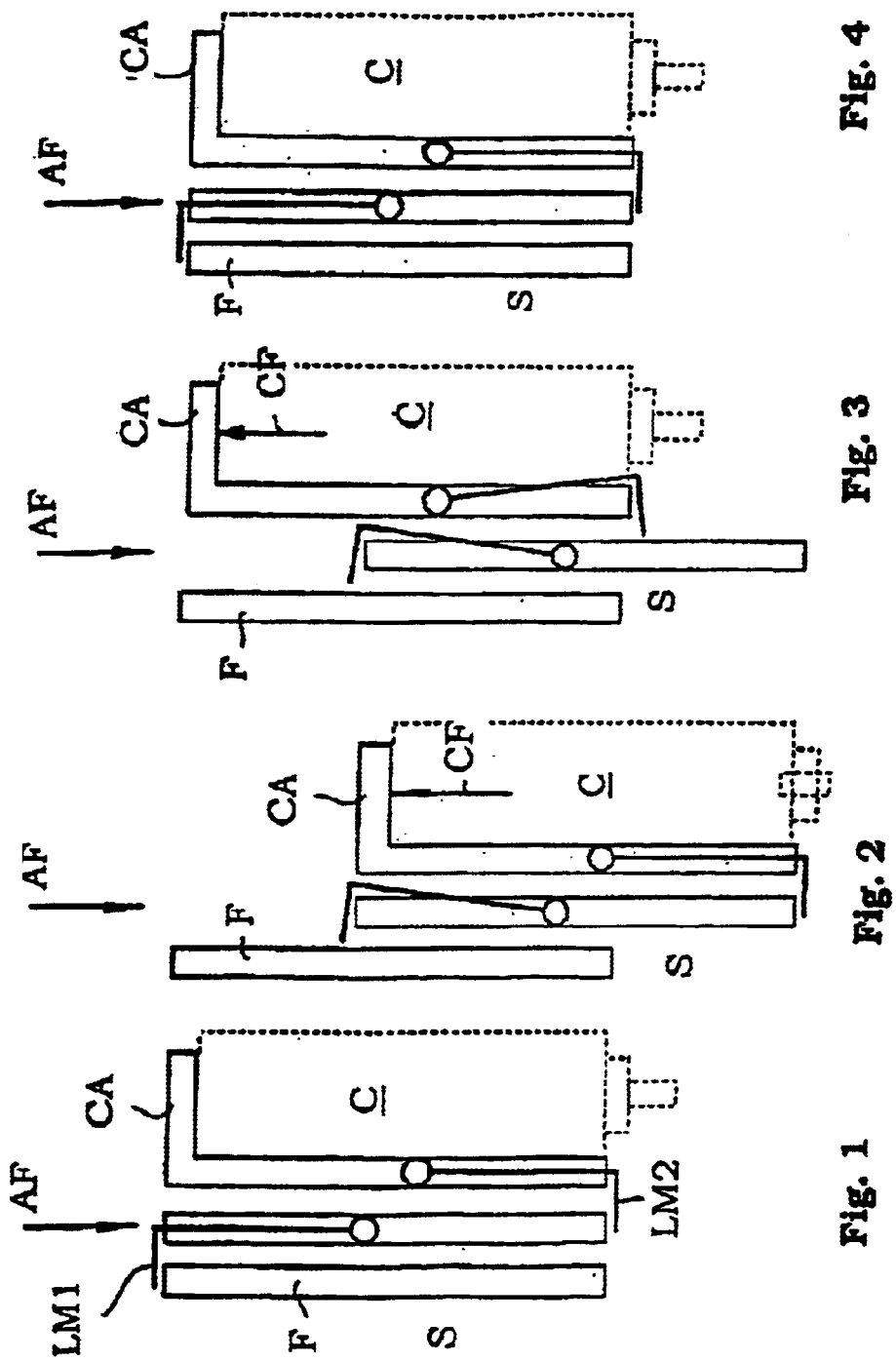

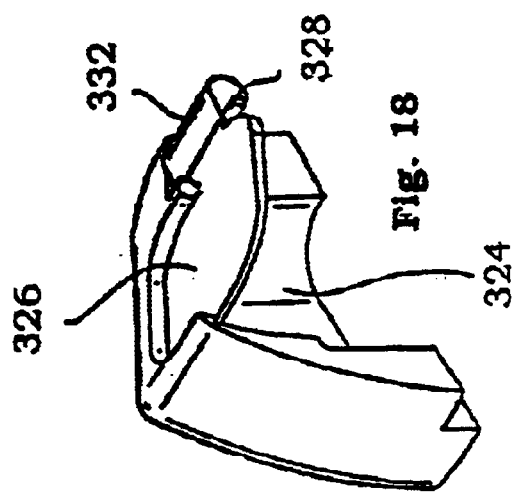
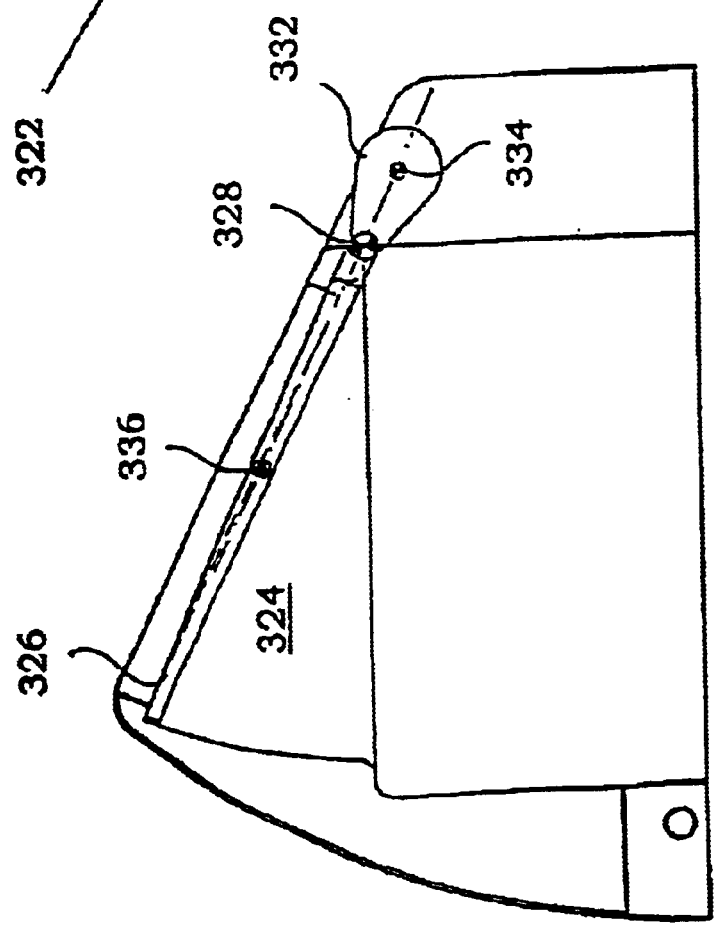

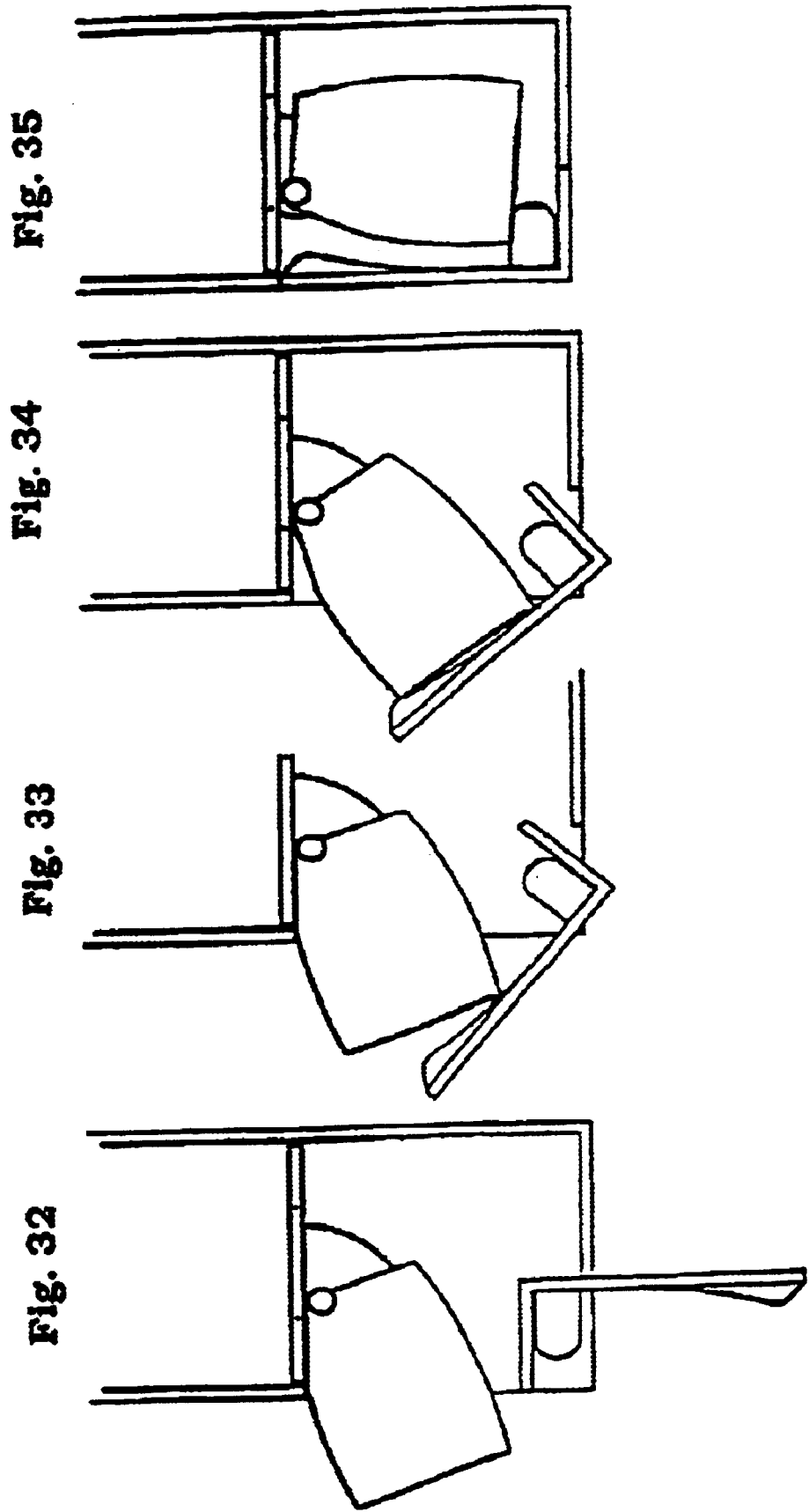

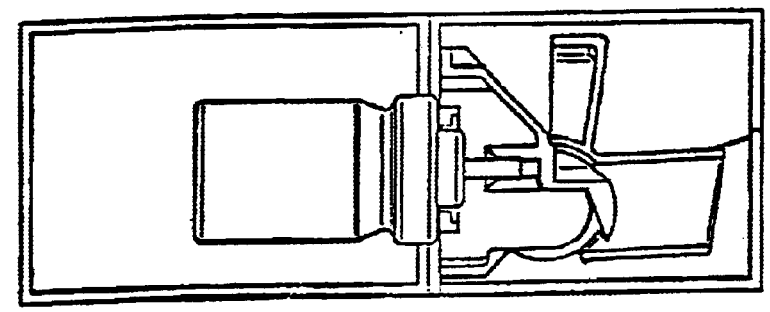
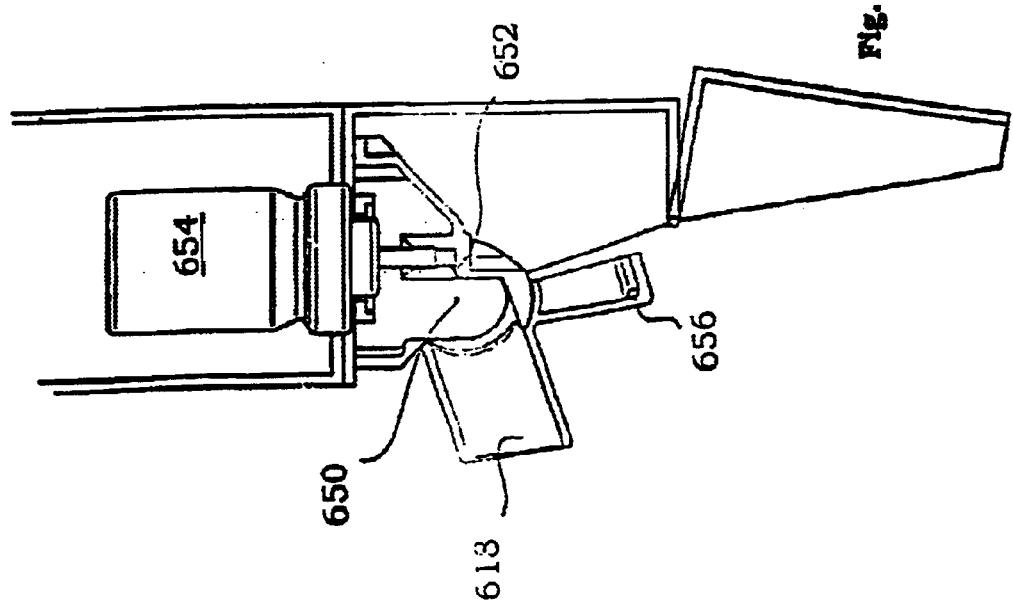
Fig. 39 even if no propellant or pressure is used. In an injector
INHALER

TECHNICAL FIELD

The present invention relates to an inhaler, the inhaler comprising a body, a compartment arranged in said body containing medicament, comprising a number of doses, which inhaler is able to dispense a metered dose of said medicament, and an opening for dispensing of said medicament.

BACKGROUND OF THE INVENTION

For a number of years inhalers have been used to deliver a metered dose of medicament to the respiratory tract of a patient. Basically there are three types of inhalers, adapted for powder medicament, aerosol driven fluid medicament and nebulisers.

The primary design of most of the inhalers are basically the same for the different forms of medicament; a housing containing a supply of the medicament, a mouthpiece, air flow conduits in connection with the supply of medicament and activating means for generating delivery of a metered dose of medicament. The activating means have a wide variety of constructions and functions. These include activation by the patients hand, such as squeezing the inhaler or maneuvering a button, during inhalation, electrically activated dose delivery, and inhalation activated dose delivery, for example.

Apart from delivery of a metered dose, most inhalers are also arranged with refilling/recharging means, that is, the chamber or compartment containing the metered dose has to be refilled/recharged after delivery, or before the next dose is to be delivered.

The drawback of the patient activated inhalers is that it may be difficult for some persons to activate the inhaler and inhale at the same instant. If these actions are not quite synchronised, the patient receives an inadequate amount of medicament into the respiratory tract. Many of the recent designs of inhalers are therefore breath activated wherein the device is activated by inhalation. This causes the canister to be depressed and deliver its metered dose.

One problem with these inhalers is that the canister remains depressed until the patient physically intervenes and removes the pressure on the canister. The chamber may not be refilled completely with these types of inhalers, especially when the amount remaining in the canister is low, because the user may hold the canister of the inhaler in a non-vertical position during the action activating/refilling of the inhalers metered dose chamber. If the level of medicament is low, it cannot then flow into the metered dose chamber in this position. Instead the chamber is filled with the propellant gas. During the subsequent dose, the patient will receive a reduced dose of medicament, perhaps only propellant gas.

Another problem with some breath-activated inhalers is that the inhaler allows for the canister to be compressed for substantial periods of time, resulting in reduced functionality of the valve mechanism.

Document U.S. Pat. No. 5,826,571 discloses a breath-activated inhaler comprising an activating means which depresses the canister in response to inhalation and return means for automatically deactivating or non-depressing the canister in response to the activating means. The inhaler further comprises control means for controlling the time the canister is open, i e the time between activation and deactivation. The return means also provides a refill of the metered dose chamber of the canister during deactivation.

One problem associated with the above inhaler is that the device controls the opening time of the canister, i e the time the canister is depressed, in order to insure that the whole dose is delivered. With the canisters presently on the market, the pressure is such that the major part of the metered dose is delivered during the first 200–300 ms after the canister opens. A remaining part is delivered during the subsequent period of time. For the previous breath-activated inhalers, the opening time posed no problem, since the canister remained open after activation until it was physically recharged. With the inhaler according to U.S. Pat. No. 5,826,571 the opening time controls the return means to deactivate the canister. A further aspect in this respect is the repeatability of the inhaler, which is one of the requirements of such a product from national authorities approving medicaments and products associated with these.

The opening time of U.S. Pat. No. 5,826,571 is controlled by a viscoelastic element. This element may be adjusted so that the required opening time is obtained when the inhaler is assembled at the factory, and even during some period of use. But repeated use, and time itself, will likely change the properties of the viscoelastic element so that the opening time varies. If shorter, the whole metered dose will not be delivered to the patient, with a deteriorated inhalation quality as a consequence due to doses delivered that are inadequate to the patient.

On the other hand, if the opening time is too long, the patient may remove the inhaler from the mouth and position it in a non-vertical position before the canister is closed and the metered dose chamber is closed. If the level of medicament then is low an inadequate refill of the chamber is obtained, as described above, and the patient does not receive its correct medicament during the subsequent inhalation.

A general problem with the known inhalers is that there is no possibility of monitoring or controlling the inhalation quality of the patient, and from that obtain an indication on the medication, since only the start of the inhalation activates the device.

Another aspect in this technical field is that many medical distribution products today have some sort of drug container comprising a number of doses of medicament and a drug delivery opening through which the medicament is delivered. For example these comprise inhalers such as aerosol inhalers where the medicament and propellant is contained in a canister or the like. The canister comprises a hollow stem through which the medicament is delivered when the stem is pressed into the canister. Other inhalers have the medicament in powder form, where the powder is contained in blisters or the like. When the medicament is to be delivered, the blister is opened, either by tearing the blister open or by piercing it so that an opening is created. With nebulisers, an ampoule or blister or other container holding the medicament is pierced or slit open.

Other medical distribution products are injectors where the medicament is contained in a syringe, which in turn is placed in a casing, which injectors automatically or semi-automatically perform different functions such as injecting the needle into the patient, delivering the medicament from the syringe and retracting the needle or ejecting a needle protector.

For the drug to be delivered from these devices, they are provided with some kind of actuating means. These often comprise springs or the like which could be "energised" i e tensioned and held in that state until they are released. The actuating means could be energised either manually by a lever, sliding button or the like tensioning the actuating means or automatically whereby they are tensioned by moving components of the device. In order to be held in an energised state, the devices comprise a locking means capable of holding the actuating means in an energised state. Depending on device, the actuating means, when released by the locking means, depress a canister, puncture a blister or ampoule or push the plunger of a syringe, etc.

The devices further comprise some sort of activating means operationally attached to the actuating means and capable of releasing the locking means when the patient is to receive a dose of medicament. These actuating means could be purely manually operated, such as a button, a lever or a handle arranged on the outer surface of the device. The patient then presses or moves the activating means in order to release the locking means.

For many inhalers, the activating means is a flap or a vane that is arranged adjacent an air intake on the inhaler and substantially blocking the air intake when not activated. When a patient inhales through an inhalation opening, a pressure difference occurs over the vane or flap. This pressure difference causes the flap or vane to move and thereby open the air intake so that an inhalation air flow is created. This movement of the flap or vane releases the locking means so that the actuating means is activated and a dose is delivered.

The spring means of the actuating means are often rather powerful. For instance with aerosol driven inhalers the spring means have to be able to depress the canister so that a dose is delivered. This means that a stem of the canister has to be pushed into the canister against the spring force of the stem and against the friction caused by the seals around the stem.

For auto-injectors there could be several actuating means. Firstly the needle has to be pushed into the patient. Then the plunger is pressed into the syringe in order to deliver the medicament. After the drug is delivered, the needle is withdrawn either by retracting it into the auto-injector housing or by pushing forward a needle protection means.

The fact that the force of the actuating means is relatively high and that it thus requires relatively high forces in order to hold or lock it in an energised state, at the same time as the forces for activating the actuating means need to be low, requires some form of transmission in order for the low activating force to be able to release the actuating force. It may be seen as one single energy system where a small input force provides a large output force.

Because of this relation, quite a number of components are required, which components will affect the energy system due to for example friction of components, tolerances and spring characteristics, giving rise to variations in force required for releasing the actuating means. Because it is one single interconnected system, the force for activating the activating means will thus also vary.

For most medical devices this is not acceptable because the activation should occur within a relatively narrow, well-defined force range. In order to cope with this, conventional techniques for these devices try to keep the number of components to a minimum and with high demands on tolerances in order to minimise the variations, in order to try to obtain predictable and repetitive conditions.

The strive to keep the number of component down and working with high tolerance requirements gives a rather costly device, by which it even so is difficult to manage all conditions.

One example is aerosol inhalers, where one, due to environmental considerations, is switching from canisters with CFC as propellant to HFA. HFA however requires much stronger seals whereby the force required to depress the canister may be substantially higher than for the CFC-canisters. With the same activating means, the variations will increase in the same degree. In order to cope with this, even higher demands on tolerances are required.

The above mentioned problems are also very much pronounced with some devices, such as multiple automatic functions acting in sequence of each other, with long and/or multiple energy systems where it is important that the forces required for triggering the different actuating means are certain to be provided without over-dimensioning the activating means. Otherwise, either it is not certain that the different functions are able to sequentially trigger each other or the device will be unnecessarily bulky and difficult to use.

According to a further aspect on inhalers, the main object with the breath-activation is to facilitate for the patient to obtain a dose of medicament, in comparison to the manually operated inhalers where the patient needs to activate the delivery by hand and inhale at the same time. This co-ordination of actions from the patient often causes problems so that, if the patient do not co-ordinate properly, the patient may not receive an adequate dose of medicament.

In the case of aerosol-driven inhalers the breath-activation causes a spring to compress a canister containing the medicament and propellant so that the medicament is delivered. Either a metered dose is delivered or the canister is open a predetermined time under which time medicament is delivered continuously. In the case of powder inhalers, the breath activation causes access to an amount of powder to be inhaled or a dose to be delivered. Other types of inhalers, such as nebulizers, may also have breath-activated devices for activating the delivery of a dose, or quantity, of medicament.

Some of the breath-activated devices comprise some form of plate-shaped lid, flap or vane movably arranged in an air flow path in the inhaler or adjacent an air intake. Upon inhalation the pressure drop and/or air flow causes the plate to move and thereby activate the actuating means so that a dose is delivered.

Some of the breath-activated inhalers are also arranged with return means. These return means "reset" the actuating means to a ready state so that the inhaler is ready for use for the subsequent inhalation. The return means also recharge the inhaler, e g refills a metered dose chamber with medicament for subsequent use. The return means are either operated manually, e g when a protective cover is closed or opened, or automatically, either at a specific time after inhalation or when the inhalation is terminated.

A drawback with the above described devices is that the breath-activated devices may unintentionally be triggered when the inhaler is ready for inhalation if the inhaler is dropped or otherwise exposed to sudden forces. Since the plates, vanes or flaps should be able to move by rather small forces exerted by the pressure drop/air flow during inhalation, they might also rather easily be moved by a sudden movement or sudden change of movement of the inhaler, such as if the inhaler is shaken or hits an object when it is ready for inhalation.

A number of doses important to the patient could be lost in this way. Further, the doses will, for many types of inhalers, be delivered inside the inhaler if triggered unintentionally. The medicament delivered inside the inhaler may deposit in passage ways or mechanisms of the inhaler and possibly obstruct the function or rendering the inhaler unclean. The deposition may also affect the dose-to-dose equivalence in that a lesser amount of medicament is inhaled than intended, and in that the deposited medicament may break loose during inhalation, whereby the amount is larger than intended.

In context with inhalers with automatic recharging means, an unintended triggering of the inhaler may also lead to an improper filling of the metered dose chamber if for example the inhaler is held in such a position during recharging that the medicament cannot properly fill the chamber. This could for example be the case with aerosol driven canisters that have to be held in a substantially vertical position when refilling the metered dose chamber, in particular when the canister is not full. The improper filling of the metered dose chamber leads to an improper dose delivered to the patient at the subsequent inhalation.

At the present, there is a wide variety of inhalers on the market, where a large quantity of these are so called aerosol-driven inhalers. These comprise a canister comprising the medicament and a gas as propellant. The canister comprises a dispensing device with a spring-loaded stem. When the stem is pressed into the canister, a metered dose of medicament is delivered.

Most aerosol-driven inhalers are provided with some activating means for depressing the canister. These span from simple levers pivotally arranged in the inhaler, which levers press on the side of the canister opposite the dispensing device, usually the bottom of the canister, to sophisticated arrangements comprising spring means acting on the canister, which springs are activated by inhalation. A recent type of inhaler also comprises motor means and control means together with a new type of canister, where the canister delivers medicament as long at it is depressed, and that the control means controls the motor which acts as depressing means for the canister. For example the control means controls the motor to keep the canister depressed for a certain period of time.

Usually, the canisters and the inhalers are manufactured by separate companies, where the canisters have different set dimensions and certain tolerance widths, and the stroke of the dispensing device has a certain stroke. On the market there are a few different canister sizes depending on the kind of medicament and the number of doses that each canister shall be able to deliver.

The manufacturers of inhalers have these canister measures to cope with when developing an inhaler, developing an inhaler for one specific canister size. Since the general aim for the developer of the inhaler is to keep the overall size as small as possible so that the inhaler is handy and discrete in use, the space inside the inhaler is rather limited. Especially when working with spring activating means it is not possible to use long springs in order to obtain a more or less constant spring characteristics during the depression movement of the canister. Instead transmission means are used to increase the spring force acting on the canister. These transmission means are however affected by differences in tolerances of the canister, of the inhaler, and of canister and inhaler together.

If, as an example, the canister has a tolerance width of a few millimeters over its entire length, which is not unusual, and the inhaler has an overall tolerance width of approximately one millimeter, this could lead to a total tolerance width of the system of several millimeters. With such tolerance widths, either the activating means will have to move quite a distance before coming in contact with a small canister, and thus exposing the canister to sudden impacts from the activating means, or, in the case of a large canister, that the activating means still contains a lot of energy when the canister is depressed. Since the starting point for the activating means varies so much with the tolerance widths built into the system and with the limited space available in the inhaler, it is very difficult to handle such differences and to design an activating means acting with the same predictable characteristics over this span.

Inhalers for inhaling medicament into the respiratory tract comprise some sort of opening, typically also with a mouthpiece, and an air flow passage inside the inhaler in communication with the opening. A compartment containing medicament and dose delivering means are also arranged and in communication with the air passage so that, when the patient inhales, air and medicament will mix in the air passage and will be inhaled by the patient.

A plurality of inhalers present on the market are provided with breath activated dose delivering means, so called breath activated inhalers. These function so as to deliver a dose of medicament when the patient inhales, i e when there is an air flow present in the air passage. In contrast to inhalers where the patient physically has to activate the dose delivering means, e g by pressing parts of the inhaler, manoeuvring levers and the like, the breath activated inhalers are triggered by the inhalation. This provides a more reliable dose delivery to the patient because the patient no longer has to time the inhalation with physical activation of the inhaler.

A drawback with these breath activated inhalers is unintentional or accidental activation of the inhaler, especially by children. A child often registers the activities of the adults and tries to do the same thing as them. If for example a parent uses an inhaler to inhale medicament, it is very likely that the child finds that interesting and would like to do the same. If the inhaler is then left within the child's reach it is likely that it would try to inhale. The inhaler would then be triggered to deliver a dose of medicament which the child unintentionally could inhale. Since these medicaments sometimes are quite potent, or even lethal, there is a risk that the child will suffer from poisoning which could lead to serious consequences.

According to yet another aspect of this technical area, inhalers for inhaling medicament comprise a body containing a supply of medicament, an air passage and a mouthpiece in contact with the air passage, wherein, upon use, the patient puts the mouthpiece in his mouth whereby a metered dose of medicament is dispensed in the air passage and inhaled by the patient.

The mouthpiece is generally a piece of pipe, either circular in cross-section or somewhat formed to correspond to the patients mouth, that is fixedly attached to, and protrudes from, the body of the inhaler.

In order to protect the mouthpiece when the inhaler is not in use, the inhaler is arranged with a protective cover or the like. In the simplest cases, the protective cover is a kind of capsule that can be pressed over the mouthpiece and is held in place by friction or snap-fit. A drawback with the capsule is that it is very easy to drop or loose it.

Most recent inhalers are provided with a protective-cover in the form of a lid pivotally arranged to the body of an inhaler. The lid is designed such that when in a protecting position, it encloses the mouthpiece protruding from the body, and when the inhaler is to be used, the lid is swung away so as to provide free access to the mouthpiece. With this design the protective means can not be dropped or lost since it is attached to the inhaler.

The general problem with the above inhalers is that the mouthpiece is fixedly attached to the inhaler body, making them rather bulky. A general desire from users is that the inhaler should be as small as possible so that it could be stored away conveniently when not in use, for example in the breast pocket or the like. This is not really the case with the present designs. Another desire from the users is that the inhaler should be easy to use in general and specifically easy and quick to activate as to inhale a dose. The activation of the inhaler may be critical if the patient suffers from a sudden reduction of the respiratory function. The inhaler must then be ready to use almost at an instant.

BRIEF DESCRIPTION OF THE INVENTION

The purpose of the invention is to provide an inhaler, without the above problems.

The primary advantage of the present invention as compared to known inhalers is that the beginning and termination, i e activation and deactivation, is controlled by the patient's inhalation and not the device, since the start of the inhalation activates the inhaler to deliver its dose and the end of the inhalation deactivates the inhaler, i e closes and refills/recharges it. This in fact increases the inhalation quality in that the end of the inhalation returns the canister to its decompressed position, during which return the metered dose chamber is refilled. This ensures refilling/recharging of the chamber when the canister is held in a vertical position with the metered dose chamber facing downwards. It's virtually impossible to have an improper refilling/recharging of the chamber when the canister has a low level of medicament, thus ensuring that a correct fill and not propellant gas enters the chamber. The inhaler could with the present invention be regarded as breath operated rather than breath activated, as with known inhalers, because both start and end of inhalation activates the inhaler.

A general aspect of the principle function of the breath operated device is that it consists of two main parts movable relative to the inhaler body. One of these is affected by an actuating or firing force from for example a spring, the first part is detachably attached to a fixed part of the inhaler, whereby the actuating force is a charged. The second part acts on a medicament delivering canister and is detachably attached to the first part. When the first part is released from the inhaler body, due to start of inhalation, it is moved by the actuating force, whereby also the second part is moved due to the attachment to the first part and the canister is depressed and a dose of medicament is delivered.

Upon end of inhalation, the second part is released whereby also the canister is released and returns to its undepressed state.

What is obtained is thus a mechanism containing relatively few components and is capable of activating and deactivating the canister in response to begin and end of inhalation.

With the use of force transmission means between the activating member, such as the flap or vane, and the actuating member, such as the compression spring capable of depressing the canister, a design with a low level of force is obtained in order to activate and deactivate the device. This ensures that patients with low physical capacities are able to activate the device. This is also an advantage in connection with the new gas propellants that due to environmental aspects are to be changed from CFC to HFA. The HFA propellants require a much higher force in order to activate the canister to deliver its dose. The device according to the invention is able of managing these higher forces without a deteriorated or reduced functionality and handling of the inhaler by the user as compared to known inhalers.

Further, with the invention it is possible in a convenient way to monitor if the patient has received the medicament in an appropriate way, by including not only dosage counters but also means for measuring the inhalation time, i.e., the time the canister has been open during delivery of a dose. This is easily obtained because activation and deactivation are triggered by the inhalation. Thus a measurement of the inhalation time can then be used to evaluate if the patient has received a dose and has been able to inhale the dose properly into the respiratory tract.

According to another aspect of the present invention the aim of the present invention is to obtain a reliable, predictable and repeatable activation of the device for delivering medicament.

This aim is solved by the present invention characterized by claim 10.

The benefit of the present invention is that repeatable and predictable handling characteristics, like for example dose-to-dose equivalence, is obtained without the need for very fine, and thus costly, tolerance demands on the components.

With the present invention, the dimensioning of the force requirements is facilitated because the energy system is divided in two distinct parts, wherein the parts, when the device is non-activated, are in no physical contact with each other. The part comprising the actuating means and transmission is designed so that the actuating means may be released with reasonable demands on design, tolerances and the like, thus allowing a certain variation in force requirements. The other part of the energy system is designed and dimensioned such that it is activated at a certain predetermined and repeatable force level, and that the force available always is above the force range required for releasing the actuating means.

Because of the division, it is not necessary to take care of the variations through the entire system, but instead merely have to calibrate the activating part of the system. Because this part mostly contains rather few components, it is necessary to design and calibrate only the activating means and the release means so that the activating means is activated at a predetermined force.

When designing this part it is also only necessary to take into account the range within which the forces required for releasing the actuating means will vary and to ensure that the force available for releasing the actuating means is substantially above this area. In this way it is ensured that the device will be activated at a certain predetermined external force level, and that the activation ensures a release of the actuating means.

It is a further object of the present invention to provide a device for the above mentioned type of inhalers which reduces the risk of unintentional triggering of the inhaler.

With a device according to the invention, the movement means, such as for example a plate or a flap, or a member of the movement means, such as a pivotally arranged linkage, or combinations of several pivotably arranged members, is held substantially stationary when the inhaler is subjected to sudden movements, but is activated, or moved, during inhalation. This prevents unintentional activation of the inhaler because of forces acting on, and trying to pivot, a member of the movement means.

Preferably the member of the movement means is balanced as regards to forces exerted on the inhaler so that the point of momentum of the member is arranged at or near its pivoting axis. This will prevent the member from being pivoted because of acceleration or retardation. With a device according to the invention, external forces on the inhaler will not trigger the breath-activated device as easily as with known inhalers of this type when the inhaler is in a ready-to-use state.

In one embodiment, when the member of the movement means is designed as a pivotable plate-like flap, a balancing means which has a moment substantially equal to the moment of the flap is arranged on the opposite side of the pivoting point. The balancing means then balances the flap so that it is held stationary when the inhaler is subject to external forces in a very simple but yet effective way.

Yet a further aim of the present invention is to allow for an inhaler to accommodate for differences in tolerance widths of containers with medicament and provide a reliable function and predictable dose-to-dose equivalence of the doses delivered. Preferably the inhaler can also accommodate for different container sizes.

With a device according to the invention the function of the inhaler is no longer influenced by the tolerance width variations of container and inhaler, which means that predictable dose-to-dose equivalence is obtained.

Further it increases the robustness and simplifies the design of the inhaler, in particular the activating means for delivering doses, since this no longer has to be over-dimensioned, such as springs, levers, attachments and the like, as the activating means no longer has to deal with the problem of tolerance variations.

Also a further aim of the present invention is to avoid the above mentioned problems concerning unintentional/accidental activation of breath activated inhalers.

The advantage of the invention over prior art is that when the safety means is not operated, any unintentional inhalation through the inhaler will not affect the activating means. Since the activating means is triggered by the air flow through the inhaler during inhalation, a manipulation of this air flow preventing the activating means to be unintentionally activated provides an easy and reliable safety device.

The blocking of the auxiliary air passage may be obtained in many different ways, for example by the finger or hand of the user, by flaps or lids or the like.

Preferably, the openings are arranged such on the inhaler, and/or have such sizes, that only an adult is able of blocking the openings in order to activate the activating means upon inhalation.

It is to be noted that the present invention may be used with all breath activated or breath controlled inhalers, regardless of type of medicament.

According to a further aspect of the invention, the purpose of the present invention is to provide a mouthpiece without the above problems.

With a device according to the invention, several advantages are obtained. Due to that the mouthpiece is arranged inside the inhaler body when not in use, the size of the inhaler can be made smaller, and also a much smoother shape can be obtained since there are no protruding parts. When the inhaler is to be used, it is activated whereby the mouthpiece is moved somewhat outside the body so as to enable the user to inhale through it.

Preferably the inhaler comprises a protective cover which protects the mouthpiece when not in use, and keeps the mouthpiece in place. Preferably also, the mouthpiece is arranged with means for releasably holding the mouthpiece in place in the activated position in a well-defined position relative the body.

When the protective cover/lid is arranged to an activating means, which sets the inhaler ready for a subsequent dose, by refilling dose compartments and placing the activating mechanism of the inhaler in a ready state, the inhaler is "charged" after a dose has been delivered to the patient. This means that the inhaler is ready to use instantly without any further actions than to open the inhaler, which is of importance during critical medicating.

Further aspects of and advantages with the present invention will become apparent from the detailed description of embodiments of the invention and from the patent claims.

BRIEF DESCRIPTION OF THE DRAWINGS

In the following description of several embodiments of the invention, reference will be made to the drawings, of which:

FIGS. 1–4 show schematically the basic function of an actuating mechanism assembly comprised in the present invention.

FIG. 18 shows a detailed perspective view, partly cut away, of a breath-activated component according to the invention balanced in two axes and comprised in the inhaler of FIG. 17, FIG. 19 shows the component of FIG. 18 from the side.

FIGS. 32-35 shows the function of the first embodiment, FIG. 39 shows an example in connection with an inhaler for aerosol driven fluid medicaments.

DETAILED DESCRIPTION OF THE INVENTION

The different features of the present invention will be described in detail and with reference to the drawings. In connection to the detailed description, use is made of "vertical" and "horizontal" to define directions of different components. It is to be understood that these directions refer to a position of the inhaler when it is used, to define the relationships between components of the embodiment described, and should not be regarded as limiting the invention.

The general principle and function of the breath operated device according to the first aspect of the invention is shown schematically in FIGS. 1–4. Here one part F is fixed in relation to the inhaler. In fact it could for example be the inhaler housing or the like. A second part, hereafter named shuttle S is movable in relation to the fixed part F. Further, an actuating or firing force AF, from for example a spring, is acting on the shuttle S. When the inhaler is in a ready-to-use state, FIG. 1, the actuating force is "charged" and the shuttle is held in the charged position in relation to the fixed part by a first movable locking means LM1. A third part, hereafter named canister actuator, CA is also movable in relation to the fixed part F and releasably attached to the shuttle S by a second movable locking means LM2. The canister actuator is arranged so that it is connected to the bottom of a canister C, which canister C in an inhaler is arranged so that its bottom is facing upwards and that its other end is provided with a valve assembly, which assembly is known per se. The canister C is pushed upwards in the figures by a spring of the canister valve assembly, causing a canister force CF.

When the inhaler is activated, in which a patient inhales, the first locking means LM1 is moved out of engagement with the fixed part F whereby the actuating force AF force the shuttle S downwards, FIG. 2. Because the canister actuator CA is locked to the shuttle S by the second locking means LM2 it is also pushed downwards against the force CF of the canister valve assembly, thereby depressing the canister so that a metered dose of medicament is delivered.

When the patient terminates inhalation, the second locking means LM2 is activated and releases the canister actuator CA, whereby the canister returns to its undepressed state and subsequently moves the canister actuator upwards.

When the inhaler is to be charged and ready for use, the shuttle S is moved upwards, for example by the patient, whereby the two locking means LM1, LM2 engage and hold the device in its ready-to-use state.

Figure 7:
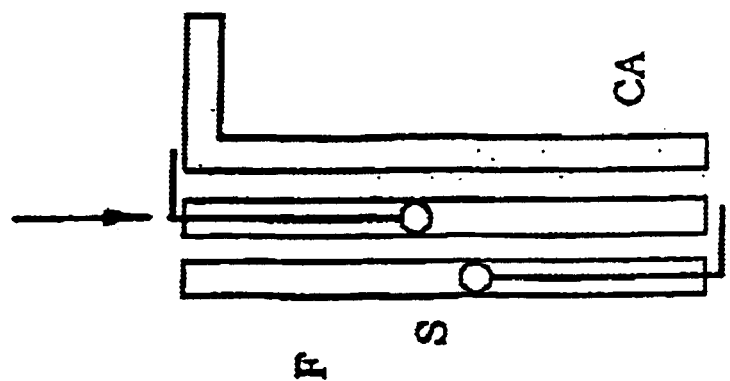
FIGS. 5–7 show different variants of the basic function according to FIGS. 1–4.
Figure 6:
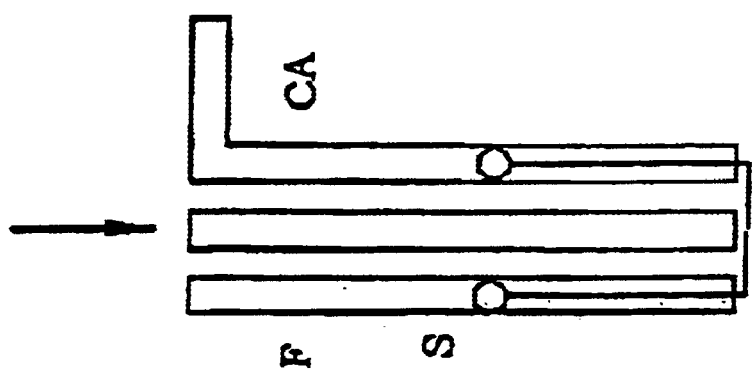
Figure 5:
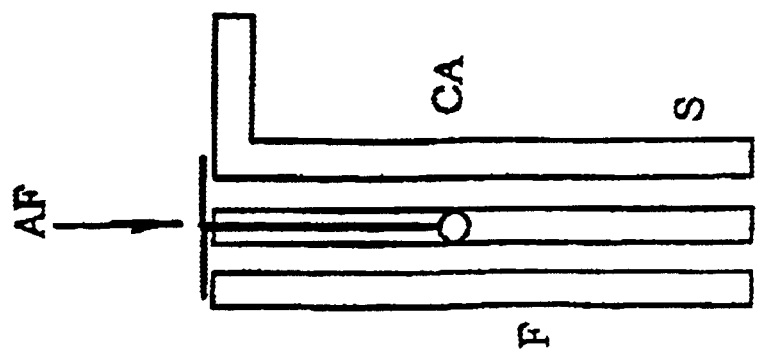

It is to be understood that the locking means may be arranged in different ways in order to obtain the desired function between the parts. FIGS. 5–7 show different arrangements. Thus the locking means could be arranged as pulling or pushing elements in order to achieve the desired function. The different elements could for example be designed as shuttles, tubular elements arranged inside each other and the like. Further, since the inhaler is breath-operated, there are requirements that the forces needed to release the locking means are quite low in order to ensure that even patients with weak respiratory capacities are capable of activating the inhaler and receiving a dose of medicament. In that respect, the device is arranged with force transmission means which enable a relatively low force to release the locking means, which in turn hold a rather strong actuating means. Examples of such force transmission means are described below.

Figure 9:
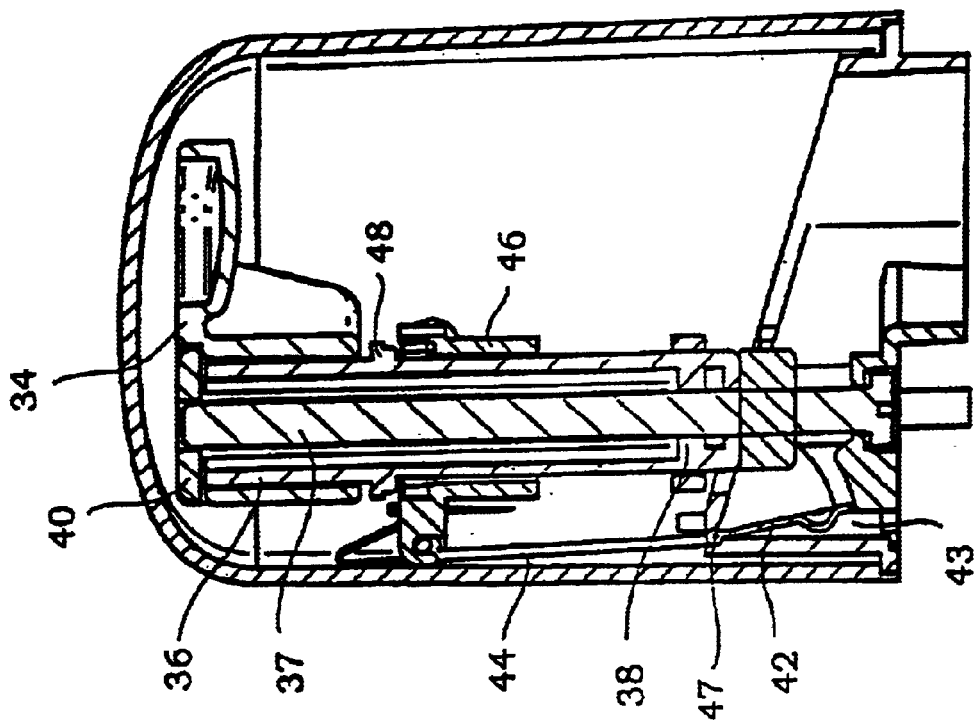
FIG. 9 is a cross section taken along the line IX—IX of FIG. 8.
Figure 8:
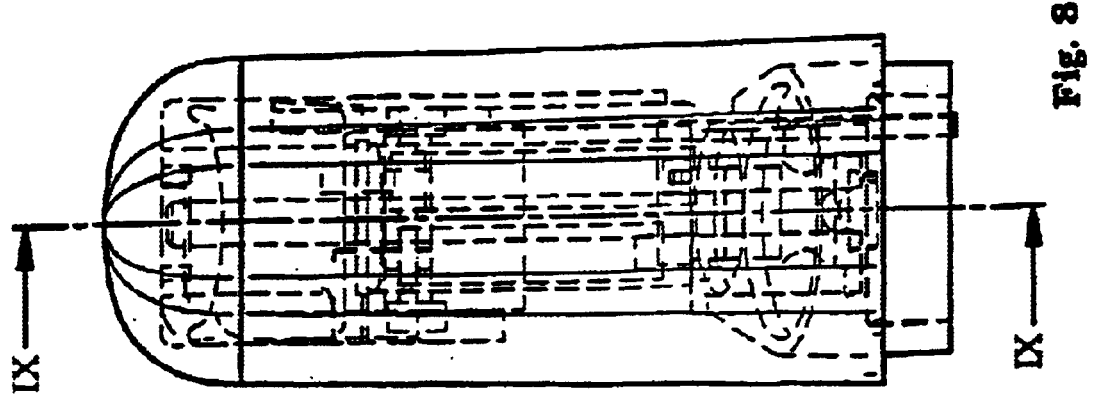
FIG. 8 shows a side view of the upper part of an inhaler comprising a device according to a first feature of the invention.

An example of an inhaling device according present invention in connection to the first feature is shown in the FIGS. 8–13. The inhaling device 10 is arranged in an inhaler, comprising a housing, in the embodiment shown in two detachable parts, where the upper part is shown in FIGS. 8–9. The upper part is arranged with a holder/chamber 18 for a metered dose aerosol container 20, hereafter named canister.

The canister, known per se and not shown for clarity, contains the medicament. It is further provided with a valve assembly in the canister comprising a valve stem, which normally is urged downwardly by a compressed spring. The valve assembly further includes a small compartment or chamber in the canister, which chamber defines the metered dose to be inhaled. The valve stem is provided with in- and outlets for filling the metered dose chamber with medicament and delivering the metered dose depending on the position of the stem in the valve assembly, as will be described in detail below.

The lower end of the valve stem is attached to, and supported by, a nozzle, which in turn is in communication with a mouthpiece. An air flow passage, not shown, is arranged from an opening on the top of the housing to the mouthpiece arranged on the housing near the nozzle.

To the upper part of the canister, an actuating means, hereafter named pressure plate 34, is arranged, abutting the bottom of the canister. The pressure plate is arranged to a cylindrical body 36 movably arranged in the vertical direction around a support shaft 37. The lower part of the cylindrical body is arranged with an inwardly projecting ledge 38. A compression spring (not shown) is arranged around the support shaft between the ledge and a fixed upper abutment 40.

Figure 11:
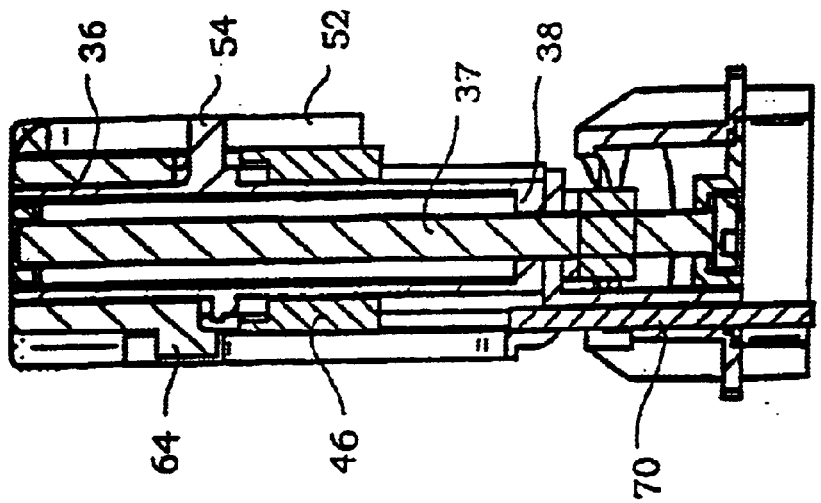
FIG. 11 shows a cross section taken along line XI—XI of FIG. 10.
Figure 10:
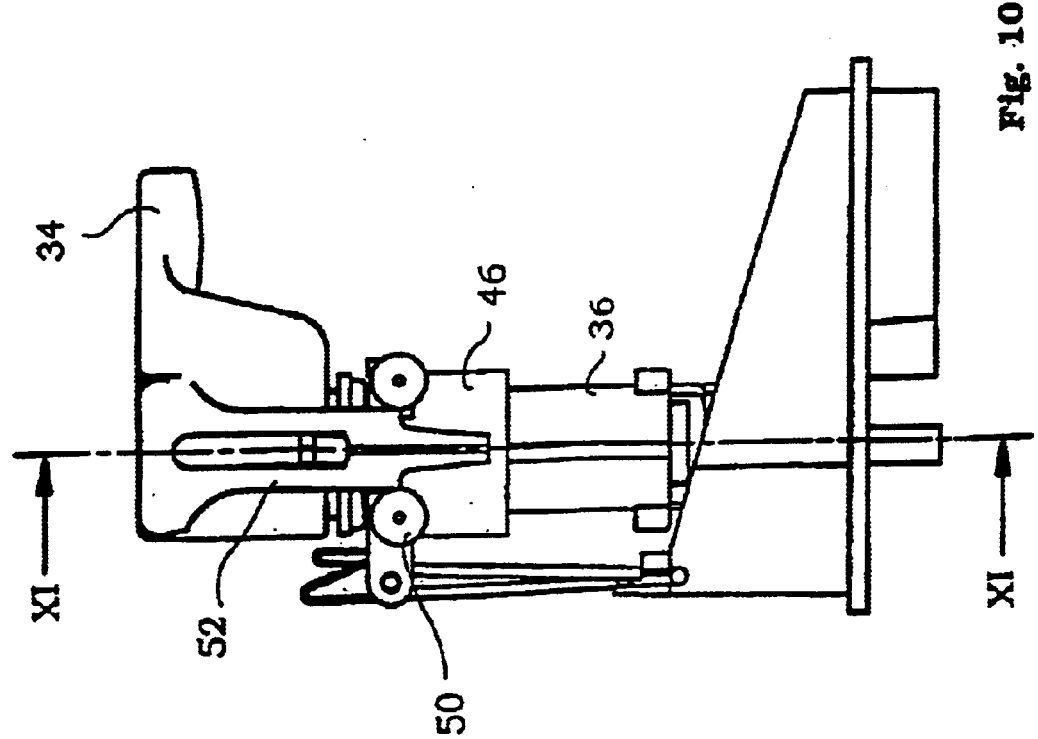
FIG. 10 is a view similar to FIG. 9 but not in cross section and with a housing removed.
Figure 13:
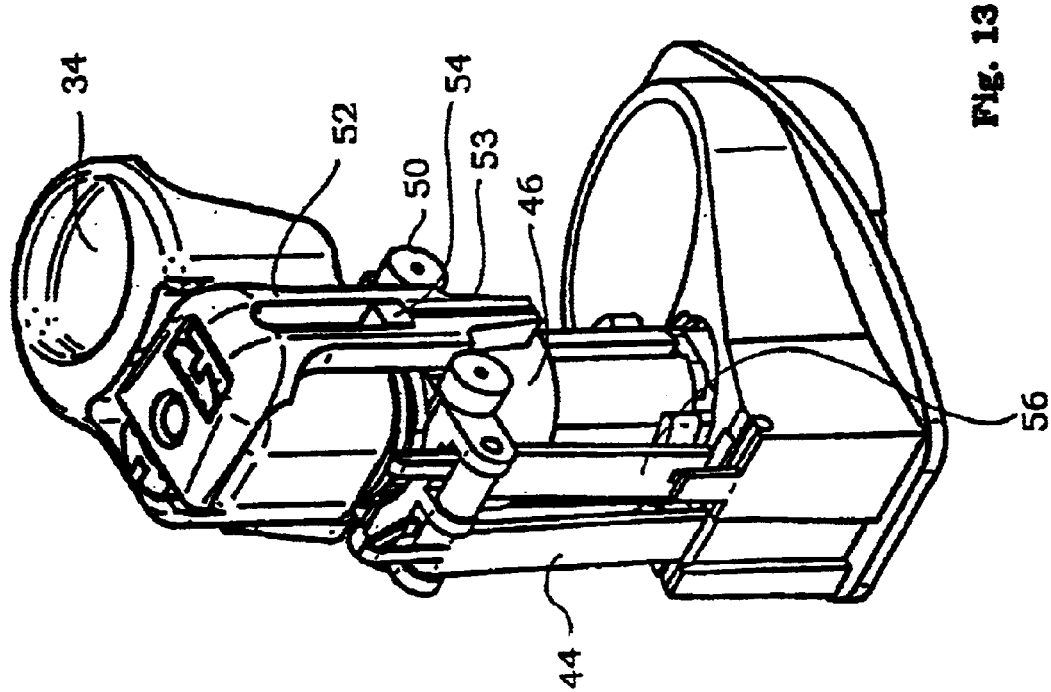
FIG. 13 is a similar view as in FIG. 12 but rotated 90°.
Figure 12:
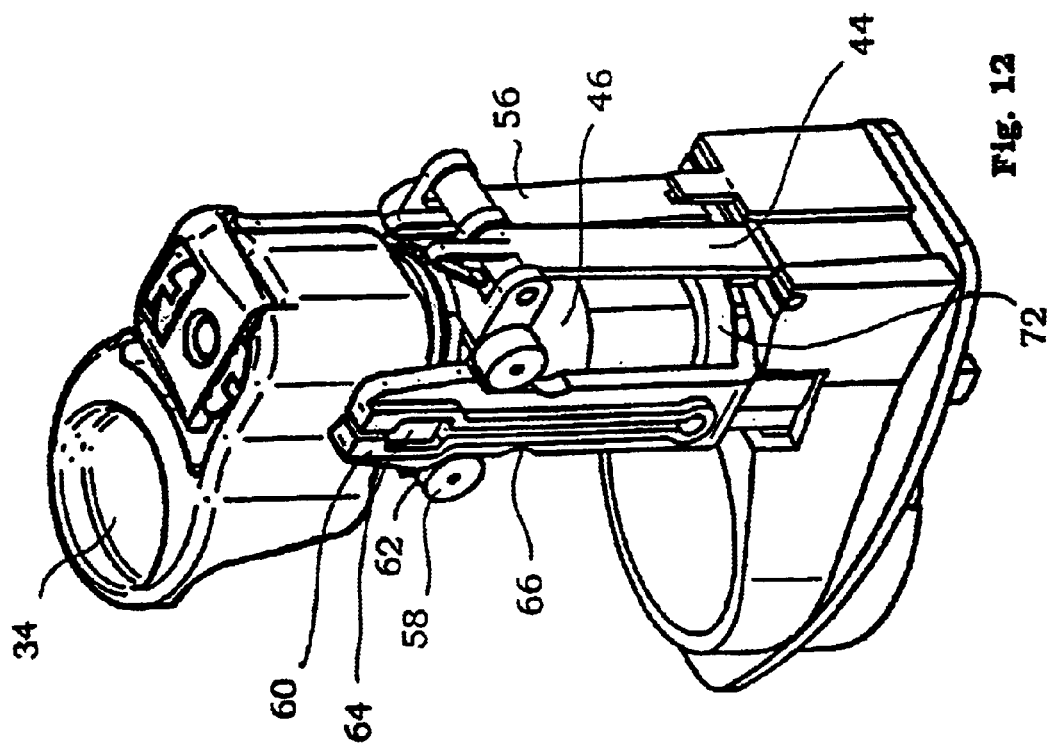
FIG. 12 is a perspective view of the device according to the invention.

The inhaler further comprises an actuator mechanism assembly. It comprises a flap 42 or vane, FIG. 9, pivotably arranged in a passage 43 in the inhaler. As shown in FIGS. 12 and 13, a first arm 44, pivotably is arranged with its upper end to a cylindrical shuttle 46. The arm 44 rests with its lower end on the flap or vane adjacent its pivoting point 47, FIG. 9. The shuttle is movably arranged around the cylindrical body, whereby the upper part of the shuttle is engaging a projection 48 on the outer surface of the cylindrical body. On the first shuttle two rotatable holding means 50 are arranged, FIG. 13. Between these a first fork-like member 52 is arranged. The fork-like member 52 is arranged with recesses 53 for receiving the holding means, as will be explained below. A pin 54 protruding from the cylindrical body, FIG. 11, is held between the forks of the fork-like member.

The shuttle is further provided with a second arm 56, arranged parallel to the first arm. The second arm is shorter than the first arm, the reason of which will be explained below.

On the opposite side of the shuttle a second set of rotatable holding members 58 are arranged, FIG. 12. Between these a fork-like member 60 is arranged, which is attached to the cylindrical body. The fork-like member has projections 62 on which the holding means rest and thereby holds the fork-like member in position. Between the forks of the fork-like member a protrusion 64 is arranged, which is attached to the pressure plate 34. Some distance downwards on the fork-like member, recesses 66 are cut out.

The function of the device is as follows. The metered dose chamber is filled with medicament in a known fashion. The shuttle has been pushed upwards by a return means so that the first arm 44 rests on the flap or vane 42. The return means comprises an arm 70 extending downwards, and connected to for example a protective cover for a mouthpiece. The upper part of the return means is designed as a ring 72 surrounding the cylindrical body 36. Between the ring and the shuttle a spring is arranged (not shown). Preferably the return means is activated when the cover is closed after use, thus activating the inhaler before the subsequent use.

When a user begins to inhale through the mouthpiece, the flap 42, arranged in the air conduit adjacent the air intake, is pivoted inwards by the pressure difference created on both sides of the flap. Due to the pivoting movement, the first arm 44 is pushed off the resting position on the flap or vane. This causes the shuttle 46 to move downwards, whereby the rotatable holding means 50 also are moved downwards until they reach the recesses 53. This enables the forks of the fork-like member 52 to move away from each other thereby releasing the pin 54 and thus the cylindrical body. The compression spring acting on the ledge 38 on the inner surface of the cylindrical body moves it and the pressure plate 34 downwards, thereby depressing the canister. Because the stem of the canister is attached to the stationary nozzle, the stem is pushed into the metered dose chamber of the canister, thereby opening the connection between the dose chamber and the nozzle. The metered dose is delivered through the nozzle and is mixed with the suction air and enters the respiratory tract of the patient.

The downward movement of the shuttle causes the second arm 56 to engage with the flap or vane and rest there. When the patient terminates the inhalation, the flap or vane is pivoted back to its original position. The pivoting movement causes the second arm to leave the rest position on the flap or vane, whereby the shuttle is moved downwards further. The second set of rotatable holding means 58 are also moved downwards, thereby permitting the forks of the second fork-like member 60 to move away from each other and release the pin 64 of the pressure plate, thus also releasing the pressure plate 34, so that the canister is returned to its undepressed by the spring of the valve assembly and the communication between the metered dose chamber and the nozzle is closed.

During the return movement from depressed to undepressed position of the canister, the metered dose chamber is refilled and ready for the next dose. It is to be noted that the refilling of he metered dose chamber always is done when the inhaler and canister are held vertically, thus ensuring refilling of the metered dose chamber with medicament, even when small amounts of medicament remain in the canister.

The inhaler could also be provided with detection and monitoring means providing information regarding the inhalation. These normally comprise counters for displaying the number of doses delivered or the number of doses that remain. With the device according to the invention, detection means for detecting the inhalation period may also be included because both the beginning and end of inhalation activates the device. The inhalation period is then an indication of the inhalation quality in the sense that if the device registers that a rather short inhalation has been done, this is an indication that the patient has not inhaled the medicament into the respiratory tract properly. The inhaler could then indicate to the user, to make him aware of this, and to suggest another dose.

The measuring points for the detection means could be any of the moving part of the device of the invention, such as the flap, the shuttles, the pressure means, and so forth.

It is to be understood that the invention is not limited to the embodiment described and shown on the drawings but may be altered within the scope of the claims.

For example, the different springs acting in the device may have different configuration and/or attachment points in order to obtain the same function. For example, the pressure means may be a vacuum bellows, known per se.

It is further conceivable to have other return means than a protective cover, like for example a button, a sleeve, lever or the like of any kind and placement. For example the upper part of the housing may be slidable in respect to the lower part in a vertical direction for activating the return means in the described way.

Figure 14:
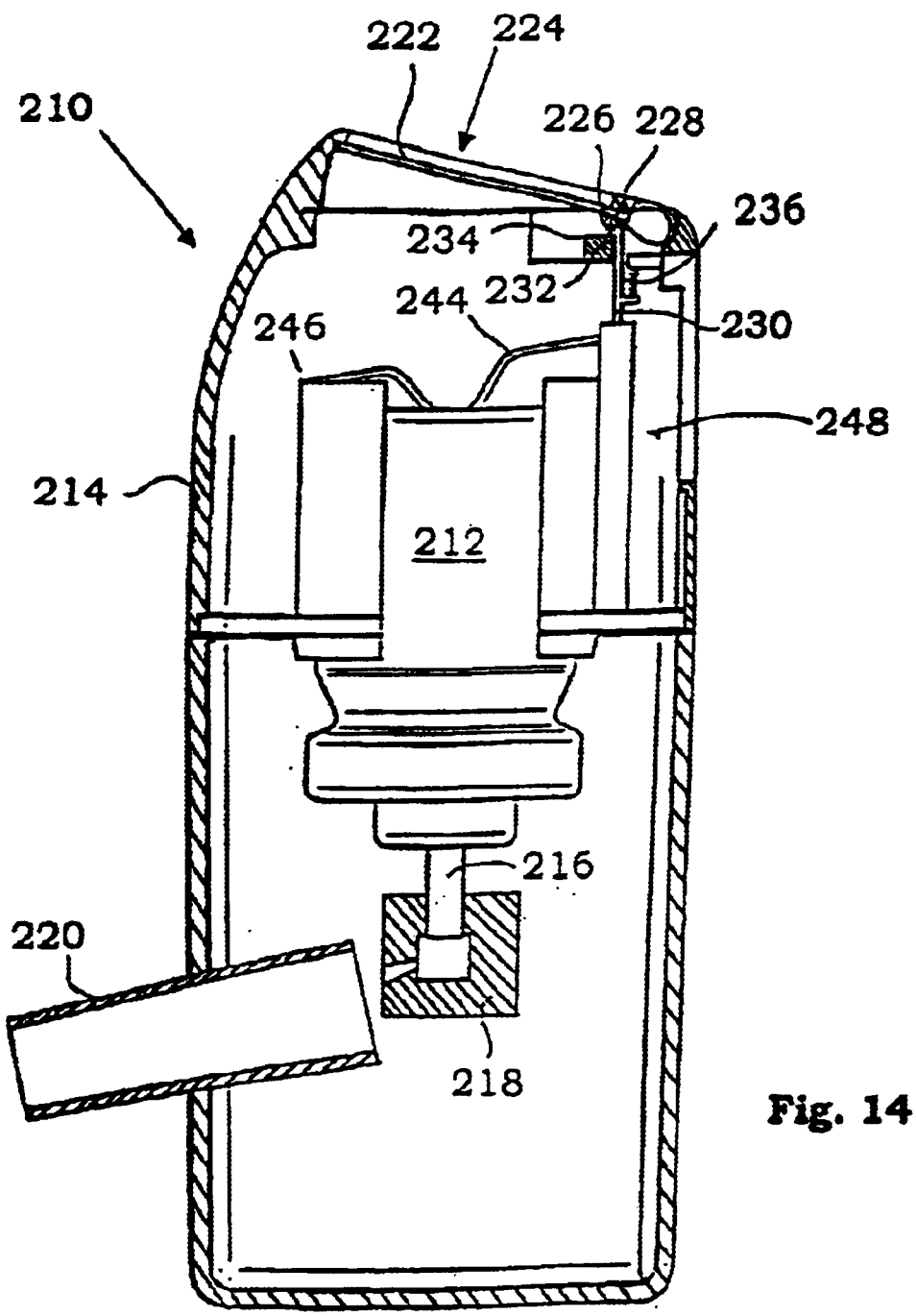
FIG. 14 shows an example of a second feature of the present invention a side view in cross-section of an inhaler comprising the present invention.

The second feature of the invention will now be described in connection with drawings 14–16. FIG. 14 shows an example of an inhaler comprising the present invention. The inhaler 210 shown is intended for aerosol-driven medicament contained in a canister 212 arranged inside the housing 214 of the inhaler. A stem 216 of the canister is seated in a nozzle 218 provided with an outlet directed towards an inhalation mouthpiece 220.

The inhaler is further provided with breath-activating means, which comprises a flap or vane 222 pivotably arranged adjacent an air intake 224 and substantially covering the intake when non-activated. The flap or vane is arranged with a protrusion 226 adjacent its pivoting point 228. A release means is arranged to the activating means, comprising an arm 230 which is arranged with a hook 232 at its upper end, which hook grips a ledge 234, in turn arranged close to the protrusion. A compression spring 236 is arranged between the arm and the housing of the inhaler. The arm extends downward into a transmission and locking means 248.

A pressure arm 244 is arranged in contact with the top of the canister as seen in the figure and pivotable around a pivoting point 246 fixed to the housing.

Figure 15:
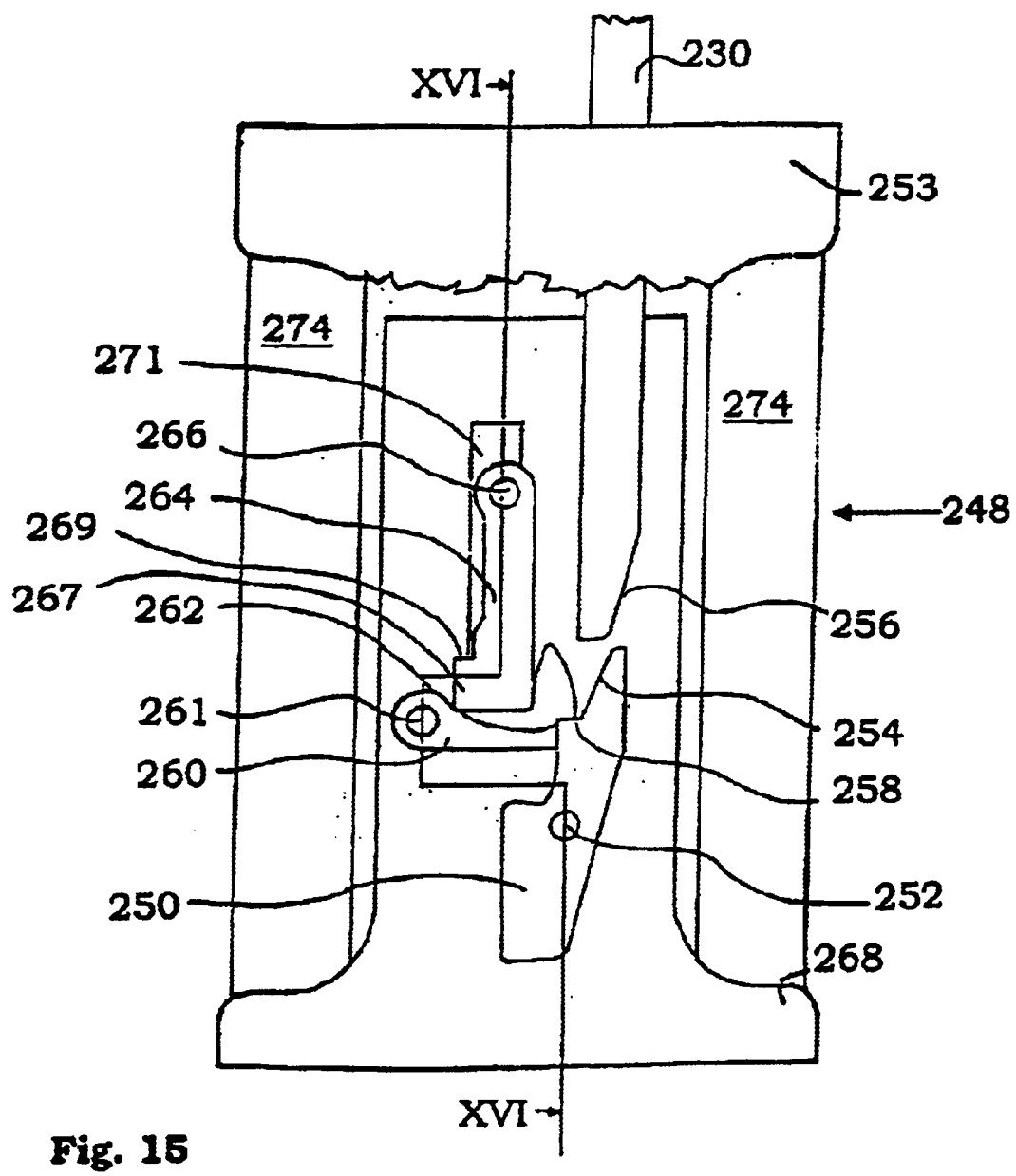
FIG. 15 shows a detailed view of a transmission and locking means comprised in the invention.
Figure 16:
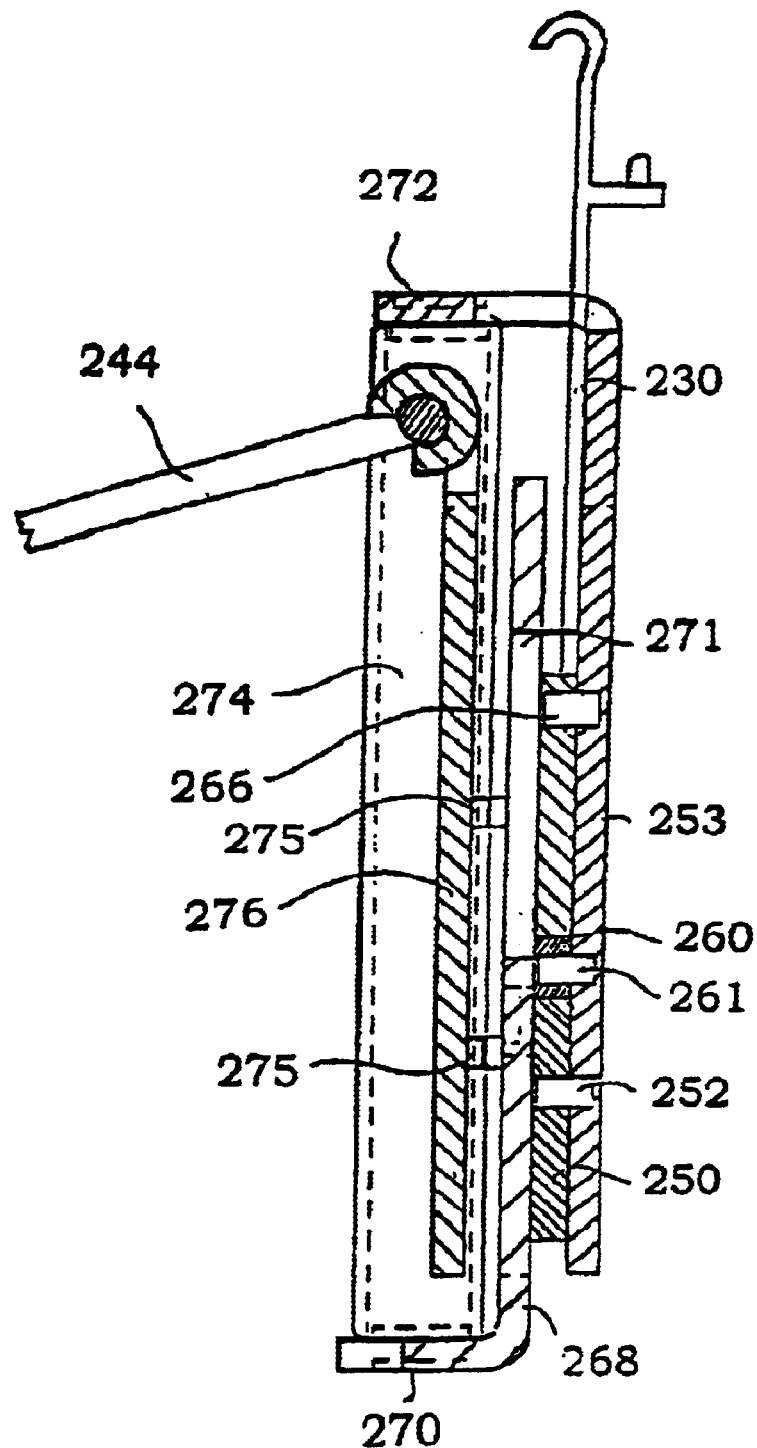
FIG. 16 shows a cross-sectional view taken along line XVI—XVI of FIG. 15

The transmission and locking means 48, FIGS. 15 and 16, comprises a first pivoting locking member 250, pivotable around an axis 252, which axis is fixedly attached to a stationary plate 253, partly taken away in FIG. 15 for clarity. The locking means is arranged with a surface 254 inclined with respect to a vertical axis as seen in FIG. 15. The lower end of the arm 230 is arranged with a mating inclined surface 256. The locking member is provided with an upwards facing ledge 258, on which ledge a first transmission member 260, pivotable around an axis 261, rests with a recess 262, thus holding the first transmission member in a substantially horizontal position. The axis 261 is also fixedly attached to the plate 253. A second transmission member 264, arranged pivotably around an axis 266 in a vertical direction rests with a lower end on the second transmission member. The second transmission member is arranged with an arm 267 whose outer end is bent inwards in FIG. 11.

The upward facing surface 269 of the arm mates with a ledge arranged in a grove 271 of a movable plate 268. The shaft 266 of the second transmission member is also attached to the plate 253. A shuttle 276 is attached to the movable plate 268 via attachments 275. The lower end of the movable plate 268 is arranged with a ledge 270. Between this ledge 270 and a ledge 272 of the stationary plate 253 are arranged two compression springs 274. An arm 276 is attached to the shuttle 268. At the upper end of the arm 276 a hook 278 is arranged. The hook grips the free end of the pressure arm 244. The transmission and locking means also comprises suitable guide means for the different components, not shown.

The function is as follows. When a patient inhales through the mouthpiece 220, a pressure difference is created between the interior of the inhaler and the outside, and thus a pressure difference over the flap or vane 222. The pressure difference causes the flap or vane to pivot around its pivoting point 228. The pivoting movement causes the protrusion 226 to push the hook 232 of the arm 230 off the ledge 234 whereby it is forced downwards by the compression spring 236. The gap between the arm 230 and the locking member 250 provides an acceleration of the arm and thus a certain dynamical force. This force provides an additional feature and advantage in designing the system and the requirements for releasing the locking member.

The downward movement of the arm 230 of the release means, due to the spring 236, causes it to come in contact with its inclined surface 256 against the inclined surface 254 of the locking member 250. The movement and the inclined surfaces causes the locking member to pivot clockwise in FIG. 15 whereby the ledge 258 of the locking member is pushed out of contact with the recess 262 of the first transmission member 260. The first transmission member is thereby free to turn downwards, whereby the arm 267 of the second transmission member 264 is moved out of contact with the recess of the groove 271. This frees the movable plate 268, which is pushed downwards due to the force of the compression springs 274, whereby the shuttle 276 is also moved downwards due to being attached to the movable plate 268 via the attachments 275. The force of compression springs is transmitted to the canister 212 via the pressure arm 244 and the canister is depressed.

As can be seen in FIG. 15, the connection between on the one hand the flap 222 and arm 230, the activating means, and on the other hand the locking and transmission means 248, transmitting the movement and actuating the delivery of the dose, the so called actuating means, is broken in that there is a gap between the arm 230 and the locking member 250. It is thus much easier to design and balance the activating means so that it is activated due to a predetermined pressure difference over the flap, and to design the compression spring 236 so that the force by the arm always is above a certain force required to trigger the rest of the system.

It is to be understood that the connection between the activating means and the actuating means is not dependent on an actual gap between the parts, as shown in the Figures. The parts may well be contacting each other. The main importance is that the operation of the activating means is influenced as little as possible by the actuating means and that it is ensured that the activating means always is capable of activating the actuating means upon inhalation. This approach enables to design the system so that care is taken of the differences in the properties of all components of the transmission and actuating means in order to have a reliable, predictable and repeatable activation of the inhaler.

In respect of the transmission described above, there could be more or fewer transmission members present depending on the forces available for triggering or unlocking the device and/or forces to be released. In this respect the transmission may also be of any mechanism capable of transferring a movement and capable of enabling a low force to release a high force.

Even though the present invention has been described in connection with an aerosol inhaler, it is to be understood that it is equally applicable to other types of inhalers such as powder and nebulisers, as well as for nasal inhalers.

Several devices of the present invention may be used in the same medical distributor in sequence, dependent, or independent, of each other. With dependent is meant that one component is moved to an end position and thereby triggers a subsequent component. With independent is meant that one component is moved to an end position. The subsequent triggering is then performed by external activation.

For example in the above example, a return means could also be provided with the same function as the above described device. This could comprise a second locking and transmission means replacing the attachments 275 between the movable plate and the shuttle 276. It comprises a further arm, which, upon termination of inhalation, is released by the flap or vane, whereby it moves the second locking means out of locking position. This causes the shuttle 276 to be released from the movable plate 268, whereby the canister is returned to its non-depressed state by the spring arranged in the canister. Return means arranged to the moveable plate 268 will push it upwards to the initial position, which for example may be done manually by shutting a hygiene lid or pushing a button.

As for injectors of the above described type, several devices according to the present invention may also be used in one injector. For instance one may be associated with the triggering of needle penetration, which is often done by pushing the syringe forward in the housing of the injector. When the syringe is in the forward position, this triggers the emptying of the syringe. This is done by springs pushing the plunger into the syringe. When the plunger has reached the dose end position or bottom and the dose is delivered, this triggers a needle retraction or a needle protection to be pushed forward. There could thus be a series of components or transmissions acting in sequence, where each sequence could make use of the "broken" connection according to the invention. With the present invention there is thus easier to take into account and deal with variations in the characteristics of the components in the chain when calculating the forces required for the reliable function of the device.

In the description both force and energy have been used in describing the present invention. It is to be understood that are equally applicable. For example releasing the locking means, a certain force may be applied to the locking means in order to move it out of locking position. In the same context, a certain energy may also applied, which for example may comprise the dynamical energy obtained by the moving release means.

It is to be understood that the embodiments described above and shown in the drawings are non-limiting examples of the present invention and that it is defined by the scope of protection of the patent claims.

Figure 17:
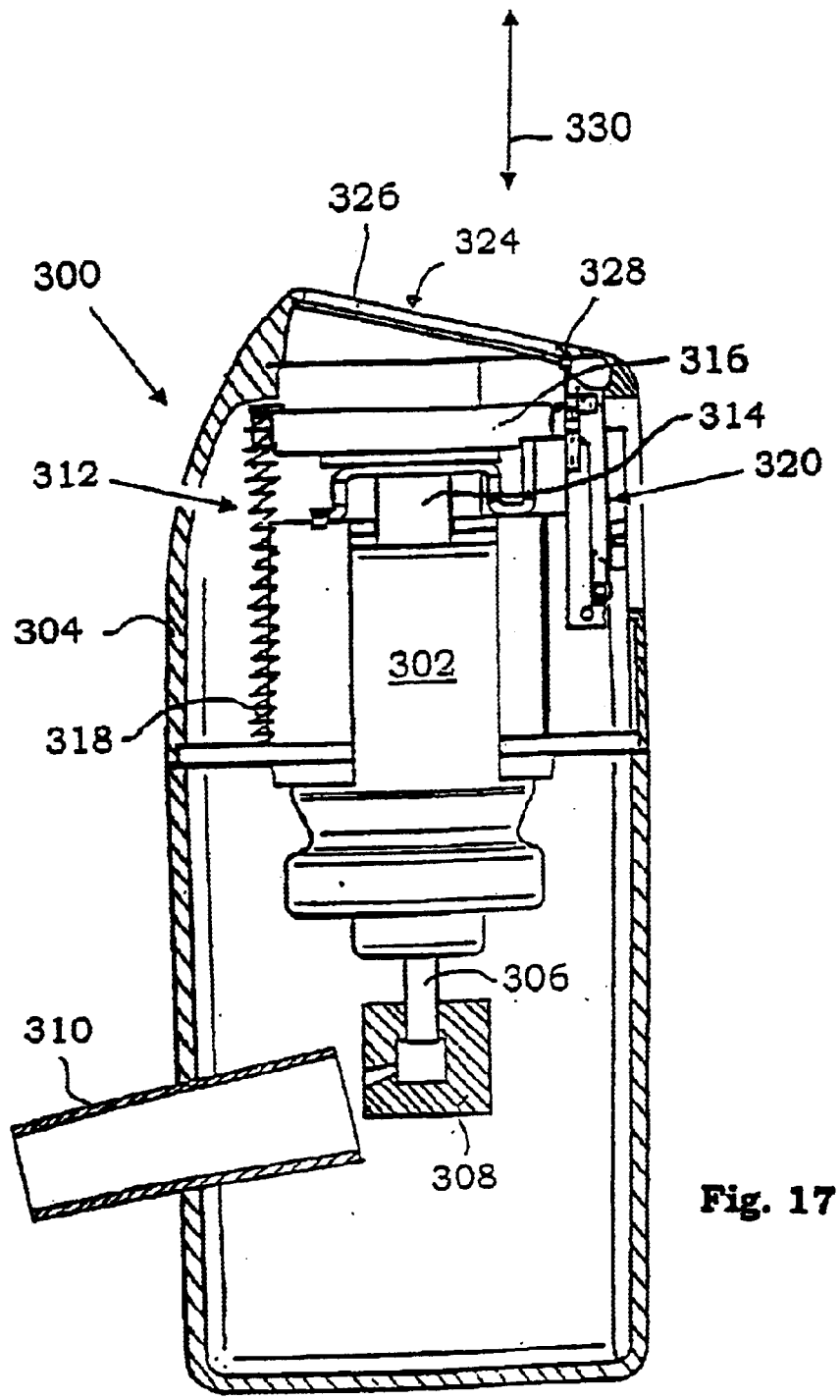
FIG. 17 shows a side view in cross-section of an inhaler comprising a third feature of the present invention.

The third feature of the present invention will now be described in connection with the drawings 17–24. FIG. 17 shows an example of an inhaler comprising the present invention. The inhaler 300 shown is intended for aerosol-driven medicament contained in a canister 302 arranged inside the housing 304 of the inhaler. A stem 306 of the canister is seated in a nozzle 308 provided with an outlet directed toward an inhalation mouthpiece 310. Pressure means 312 is arranged in contact with the top of the canister as seen in the figure. The pressure means comprises a piston 314 and a pressure plate 316. Compression springs 318 are arranged between the pressure plate and the housing. Actuating means 320 are arranged in connection with the pressure plate for holding it in a position where the compression springs are tensioned. The actuating means further comprise levers and shuttles.

FIG. 18 shows a detail of a component 322 of a breath-activated inhaler. The component comprises an air intake passage 324, through which air flows during inhalation. In the air intake a flap or vane 326 is arranged pivotably around a pivot axis 328. Spring means (not shown) urges the pivot upwards in FIG. 18 against the interior wall of the air intake. In this position the flap or vane substantially blocks the air intake passage. The part of the vane opposite the pivoting axis is connected to the actuating means 320.

The general function of the component is that during inhalation, a pressure difference is created between the interior and the exterior of the inhaler housing 304. This pressure difference causes the flap or vane 326 to pivot around the pivoting axis 328 against its spring means so that the air intake opens and an air flow is created. The pivoting movement of the flap or vane triggers the actuating means so that the hold of the pressure plate 316 is released whereby the springs 318 depresses the canister 302. In turn the stem 306 is pushed into the canister whereby a dose of medicament is delivered through the mouthpiece 310.

The flap or vane is arranged with balancing means 332. In the embodiment shown in FIGS. 18 and 19 it comprises a weight arranged on the opposite side of the pivoting point in relation to the flap or vane. The centre of mass 334 of the weight is arranged in the same plane as the centre of mass 336 of the flap or vane and the pivoting point. The weight of the balancing means is chosen such that the weight times the distance to the pivoting point equals the weight of the flap or vane times the distance between its centre of weight and the pivoting point. With this arrangement the flap or vane is balanced as regards external forces exerted on the inhaler in that the resulting moment on both sides of the pivoting point is the same. Since the centres of mass are placed in the same plane as the pivoting point the flap or vane will be balanced for external forces in all directions.

Figure 20:
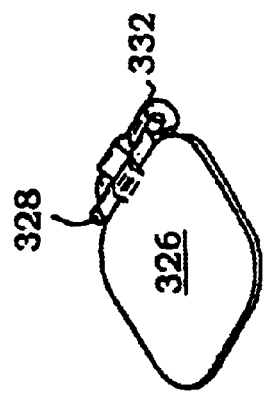
FIG. 20 shows a detailed perspective view of a flap comprised in an inhaler, balanced in one axis.
Figure 22:
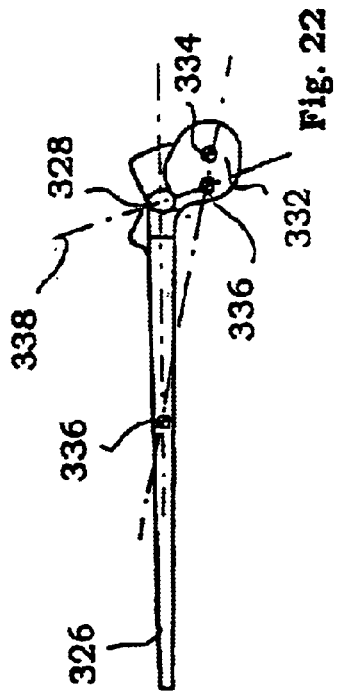
FIG. 22 shows a side view of the flap of FIG. 20.
Figure 21:
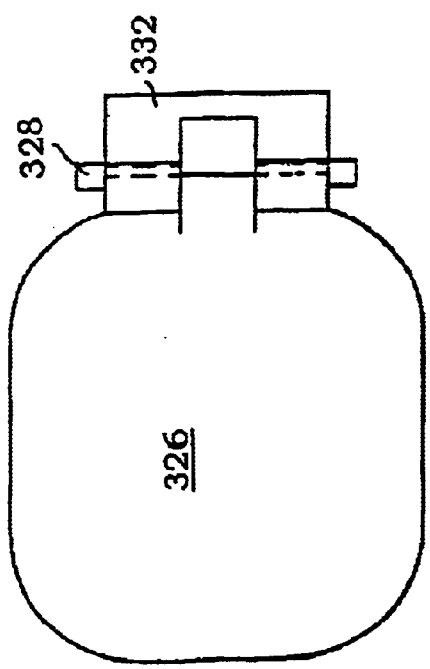
FIG. 21 shows a plan view of the flap of FIG. 20.

FIGS. 20–22 show an embodiment where the flap or vane 326 is not balanced in all directions. Here the weight 332 is placed somewhat below the pivoting point and the flap or vane. Here the centres of mass 336 of the flap or vane and the balancing means 334 and the pivoting point 16 will not be arranged in the same plane. Here the flap or vane will be substantially balanced along the line 338 intersecting the pivoting point and the resulting centre of mass.

This configuration may be due to the limited space available in the inhaler. The resulting centre of mass 336 will thus not coincide with the pivoting point of the flap or vane but with the line 338. It is however arranged such that the flap or vane is balanced for forces exerted on the inhaler in selected directions. For example with an aerosol inhaler it is recommended that it is shaken before use so that the medicament inside the canister is properly suspended. Depending on design of the inhaler, i.e. how it is held, it is shaken in certain directions. The inhaler shown in FIG. 17 will be shaken substantially in the vertical direction as shown by arrows 330. The flap or vane is then substantially balanced with respect to those directions.

Figure 23:
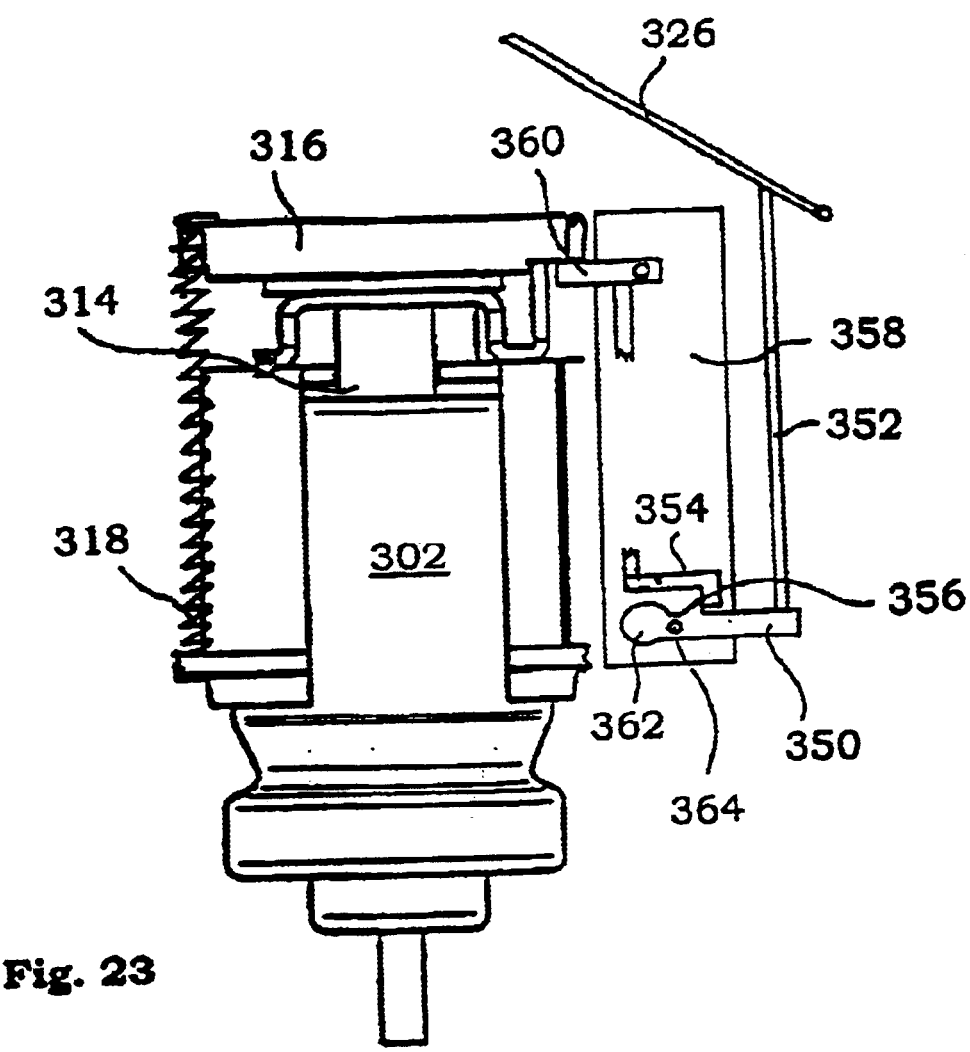
FIG. 23 shows a detailed view of another use of the present invention.

FIG. 23 shows another use of the present invention. For many inhalers it is important that the inhalation forces are kept low, making it necessary to have the actuating means respond to these low forces. On the other hand the depression forces need to be rather high in order to be capable of overcoming the forces for depressing the canister. Therefore, it is necessary with some kind of transmission mechanism which amplifies the movement from the flap or vane to the compression springs. FIG. 23 shows one example of how the first link or the transmission comprises a lever 350 pivotably arranged.

The lever is connected to the flap or vane 326 via a piston 352. A second arm 354 or lever is connected to the lever via a ledge 356. The transmission 358 comprises further arms, levers, pistons, shuttles and the like in order to transmit and transfer the movement to a holding means 360 holding the pressure plate 316 against the force of the compression springs 318. When a patient inhales, the flap 326 is pivoted around its pivoting axis whereby the piston 352 is pushed downwards. The piston pivots the lever 350 whereby the arm 354 disconnects from the ledge. The movement is transferred through the transmission until the holding means 360 releases the pressure plate. Because very small forces are needed, and desired, in order to pivot the lever, it is balanced against external forces according to the invention. A weight 162 is arranged on the opposite side of the pivoting point and chosen such that the resulting centre of mass of the weight an the lever coincides with the pivoting point 364, whereby the lever is balanced against directed forces, for example vertically as seen in FIG. 23.

Figure 24:
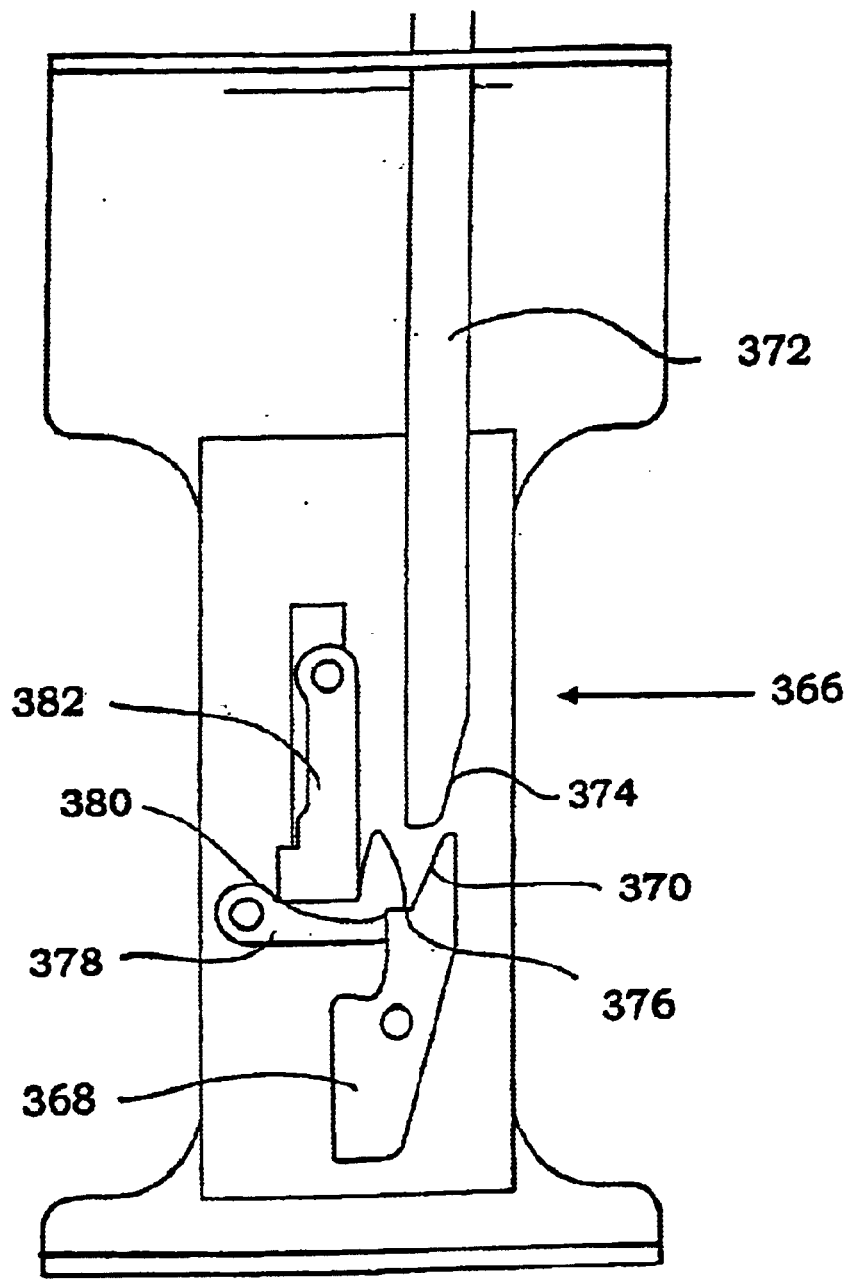
FIG. 24 shows a detailed view of a further use of the present invention.

FIG. 24 shows a detailed view of a locking and release means 366 for a breath activated inhaler. It comprises a first pivoting member 368 pivotable around an axis. The first member is arranged with a surface 370 inclined with respect to a vertical axis. The lower end of an arm 372 arranged to a breath activated member, not shown, is arranged with a mating inclined surface 374. The first member is provided with an upwards facing ledge 376, on which ledge a second pivotable member 378 rests with a recess 380, thus holding the second member in a substantially horizontal position. A third member 382, arranged suitably in a vertical direction rests with a lower end on the second member. The third member is attached to a holding member, which holds for example pressure springs arranged to a canister of an inhaler in an energised, tensioned state. As soon as the arm 372 is moved downward, whereby the subsequent members are brought out of contact with each other, the canister is depressed by the force of the springs. In order for the inhaler not to be activated by sudden forces, the first member 368 is balanced so that its centre of mass is placed in the pivoting point of the member.

Even though the present invention has been described in connection with an aerosol inhaler, it is to be understood that it is equally applicable to other types of inhalers such as powder and nebulisers, as well as for nasal inhalers working with the same principles.

It is to be understood that the present invention may be used for balancing statical as well as dynamical forces, i e predetermined directions of movement, non-predetermined directions of movement as well as movements in several planes.

Even though the invention has been explained in connection with a balancing means arranged to the flap and lever of the transmission mechanism, it is to be understood that the principles of the invention may be utilised for other components of an inhaler which are pivotably arranged.

In this context it is to be understood that the wording "pivotably" may be members balancing on an edge, or that the shaft on which a pivoting member is arranged is smaller than the hole, so that there is one specific contact point, pivoting point, between the shaft and the hole.

Figure 25:
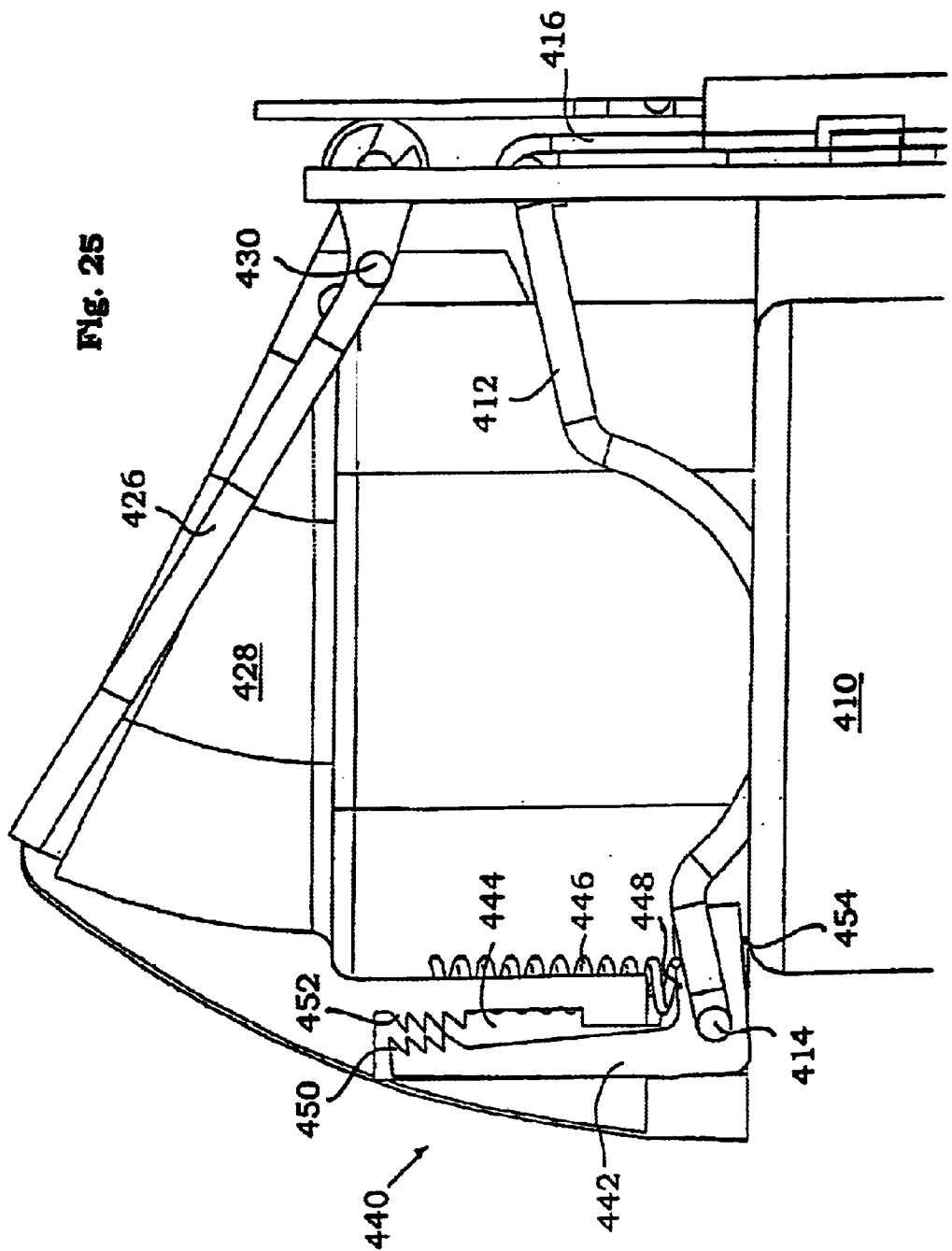
FIG. 25 is a detailed view of a part of an inhaler comprising the device according to a fourth feature of the present invention in a non-active position.

The fourth feature of the present invention will now be described in connection with FIGS. 25–27. In the drawings parts of an inhaler for aerosol-driven medicament with breath-activated dose-delivering means is shown. The medicament and the aerosol as propellant are stored in a canister 410 where the upper part is shown in the drawings.

In a conventional manner, the canister is arranged with a stem containing a passage at its lower part. The stem protrudes inside the canister, and when the canister is depressed a dose of medicament is delivered through the passage of the stem. Also in a conventional manner, the stem communicates with an inhalation opening, through which the dose is delivered. These parts are not relevant to the invention and are therefor not shown for the sake of clarity.

A depressing means is arranged at the upper part of the canister. In the embodiment shown it comprises a pivotally arranged lever 412 with a portion that is curved downwards somewhat corresponding to the concave shape of the canister end wall. At the opposite end to the pivoting point 414 of the lever, a depression means is arranged, comprising a compression spring (not shown) attached via an arm 16 to the end of the lever.

Above the spring means, an activating means is arranged comprising a flap 426 pivotally arranged in the inhaler in an air passage 428 communicating with the exterior of the inhaler. The shape of the flap and the passage is such that the flap substantially closes the passage when it is in its uppermost position, FIG. 25. The flap is connected to the depression means.

When a patient inhales in order to receive a dose of medicament, the inhalation causes a pressure difference between the interior of the inhaler and the exterior. This pressure difference causes the flap 246 to pivot and the passage 428 to open so that an air flow is created. The pivoting movement of the flap acts on the depression means so that the compression spring pulls the arm 416 downwards whereby the lever 412 is pivoted downwards. The pivoting force depresses the canister 410 so that a dose of medicament is delivered.

An adjustment means 440 according to the invention is also arranged in the inhaler. It comprises a generally L-shaped member 442 arranged in a compartment 444 and movable in a vertical direction. The lower branch of the L-shaped member protrudes somewhat over the end wall of the canister. The lever 412 is pivotally arranged to the lower branch of the L-shaped member adjacent the intersection point with the upper branch. A vertically acting compression spring 446 is arranged between the inhaler housing and the lower branch of the L-shaped member, where the contact point 448 of the spring is somewhat closer to the canister than the pivoting point 414 of the lever. The upper branch of the L-shaped member is provided with a number of teeth 450 arranged on the surface facing inwards. The opposite surface of the compartment is provided with a number of corresponding teeth 452.

When a canister is inserted in the inhaler, the end wall will come in contact with the lower branch of the L-shaped member 442, thereby pushing it upwards somewhat against the force of the compression spring 446. Because the contact point 454 between the L-shaped member and the canister is further out on the lower branch of the L-shaped member than the contact point 448 of the compression spring, the L-shaped member will be tilted somewhat outwards in FIG. 25 when the member is moved upwards by the insertion of the canister. Because of the tilting, the teeth of the upper branch and the compartment are not in contact with each other, FIG. 25.

Figure 26:
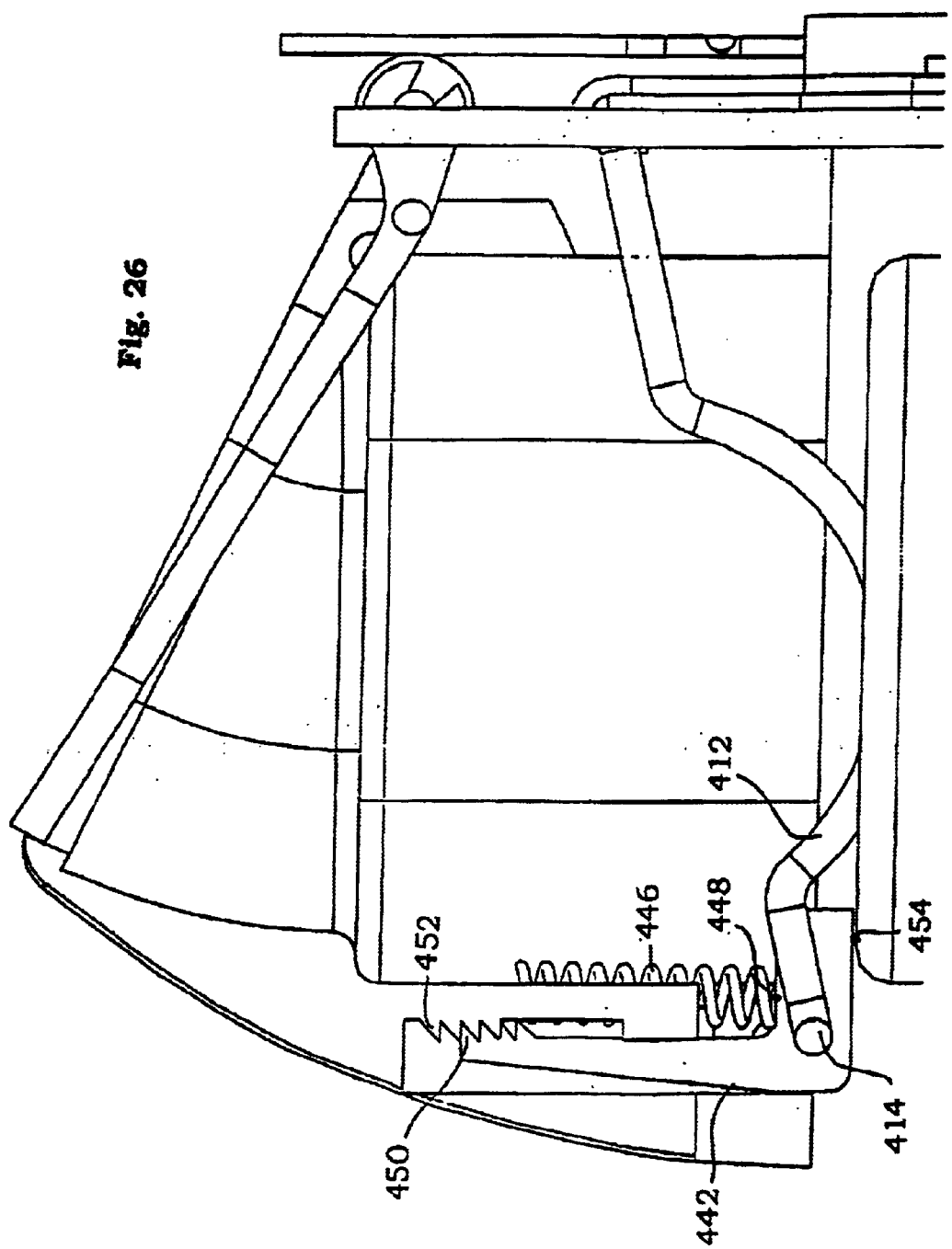
FIG. 26 is the same view as FIG. 25 with the device in an active position.
Figure 27:
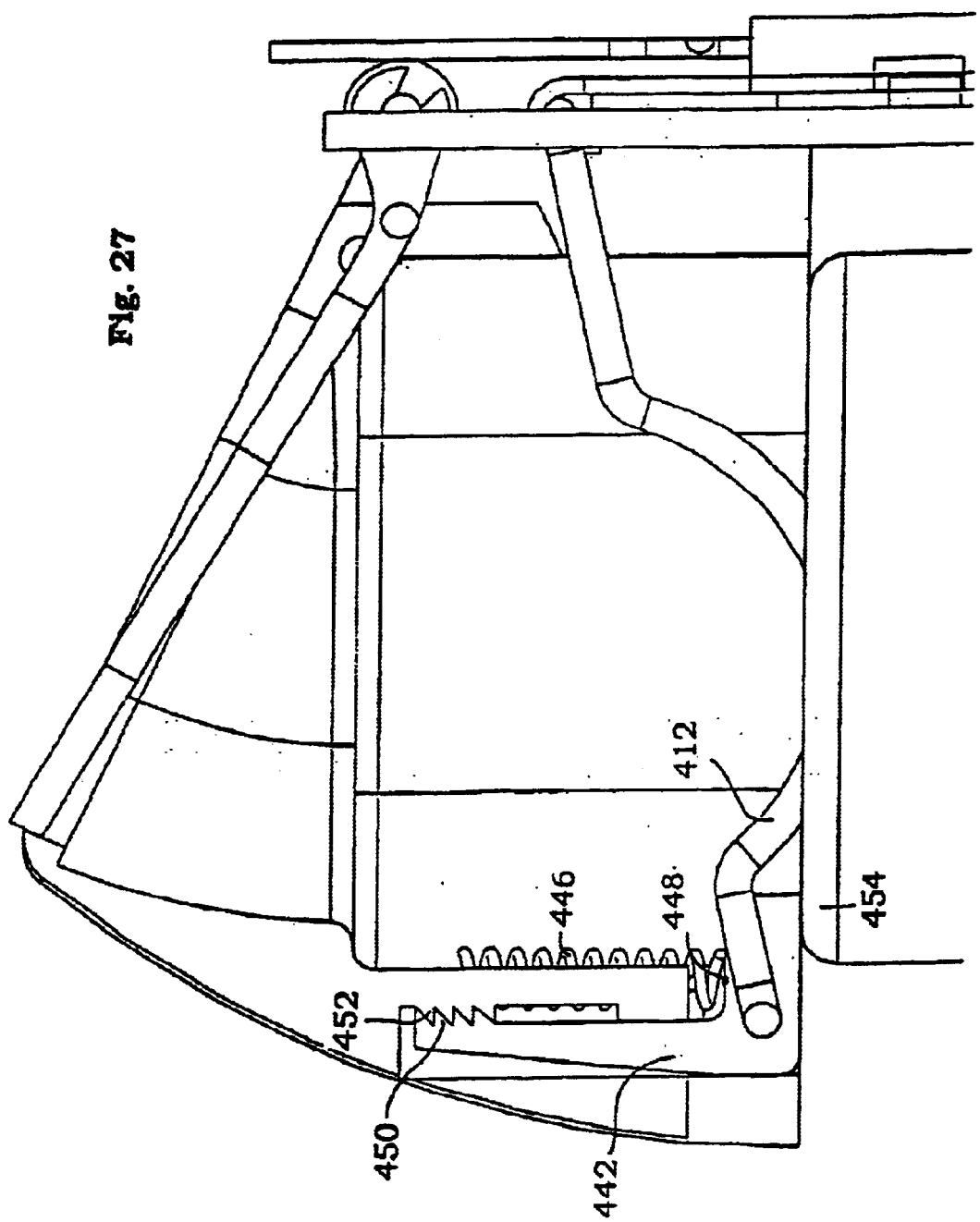
FIG. 27 is the same view as FIG. 25 with the device in another active position.

When the lever is activated upon inhalation, the upwards directed reaction force on the lever at its pivoting point 414 will cause the L-shaped member to pivot around the contact point 448 of the compression spring and the teeth of the upper branch of the L-shaped member and the teeth of the compartment to engage with each other, thereby fixating the vertical position of the member and in turn the position of the pivoting point of the lever, FIG. 26. The adjusting of the pivoting point of the lever by using the end of the canister as a "reference point" ensures a constant and reliable relation between the two with more or less the same angle of the lever in relation to the canister end wall, regardless of differences in tolerances of the different components, i e the canister, the inhaler or both, FIG. 27. With the device according to the invention variations in the order of 10–20% of the length of the lever can readily be handled.

It is to be understood that although the adjusting member is shown with an L-shape where the branch with teeth is facing upwards, this member could be facing downwards with the teeth on the other side of the branch and corresponding teeth on an opposite surface. Further, other configurations of the member are conceivable for obtaining the same function of the height adjustment. Also fixating means other than teeth could be used.

In this context it is conceivable to have an adjusting means with the same function, and also using the end wall of the canister as a reference together with the spring means. If the spring means also is adjustable in height, the adjustment span could accommodate for canisters with larger differences in size than tolerance differences.

Figure 28:
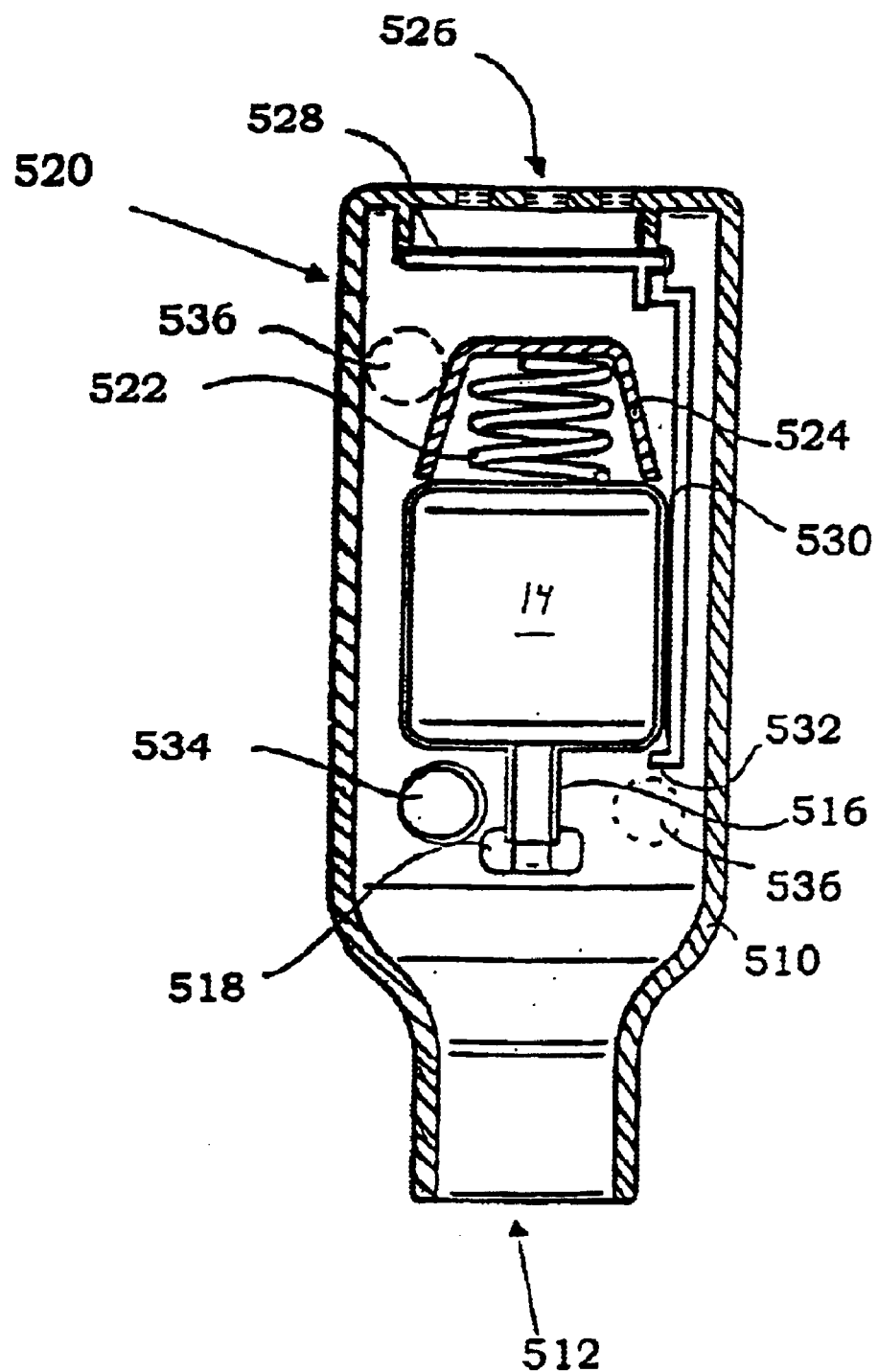
FIG. 28 shows a side view in cross-section of an inhaler for aerosol-driven medicament with a device according to a fifth feature of the invention.

A fifth feature of the present invention will now be described in connection with FIGS. 28–29. FIG. 28 shows, as an example, an inhaler for aerosol-driven medicament which may utilise the present invention. The inhaler comprises a housing 510 with an opening 512 intended for inhalation of a dose of medicament. Inside the housing is arranged a canister 514 containing the medicament and aerosol as propellant. The canister is provided with dose delivery mechanism comprising a spring-loaded stem 516. The stem is provided with a passage extending into the canister. The stem/lower part of the canister is supported by a holding/fixating device 518.

At the opposite end of the canister stem, an activating means 520 is arranged. It comprises in the embodiment shown a spring 522 with one end pressing on the canister and the other end supported by a holder 524.

The activating means further comprises an air inlet 526 arranged in the inhaler housing and a flap 528 pivotally arranged adjacent the air intake. When the flap is in a resting, inactivated, position, it covers the air intake. Arranged in contact with the flap is a holding means 530, which in the embodiment shown comprises an elongated arm extending alongside the canister side. The arm is at its lower end arranged with a ledge 532. When in a resting position, the arm and the ledge holds the canister in an inactivated position against the force of the spring. The interior of the inhaler, from the inhalation opening to the air intake forms an air passage.

The inhaler further comprises a safety means. It comprises at least one auxiliary air intake 534 arranged to communicate with the inhaler air passage, forming an auxiliary air passage with the inhalation opening, where the intake is positioned between the inhalation opening and the flap/main air intake. Further auxiliary air intakes 536 are shown with broken lines.

In normal use of the inhaler, without the safety means, the start of an inhalation through the inhalation opening causes a pressure difference between the interior and the exterior of the inhaler. This pressure difference causes the flap to pivot, thereby causing an air flow through the inhaler from the air intake to the inhalation opening. The pivoting movement of the flap acts on the elongated arm so that the arm is swung away somewhat from the canister. This causes the ledge to release the canister from its inactivated position. The force of the spring causes the canister to depress whereby the stem is pressed into the canister and a dose is delivered to the inhalation opening, which dose is inhaled by the patient.

When the safety device according to the invention is used with the inhaler and the auxiliary air intake is closed, the function is as described above.

If on the other hand someone tries to inhale without closing the auxiliary air intake, an air flow passage is created from the auxiliary air intake to the inhalation opening, thereby preventing a build-up of a pressure difference inside the inhaler. Because no pressure difference is created, the flap will not be affected by the inhalation.

Figure 29:
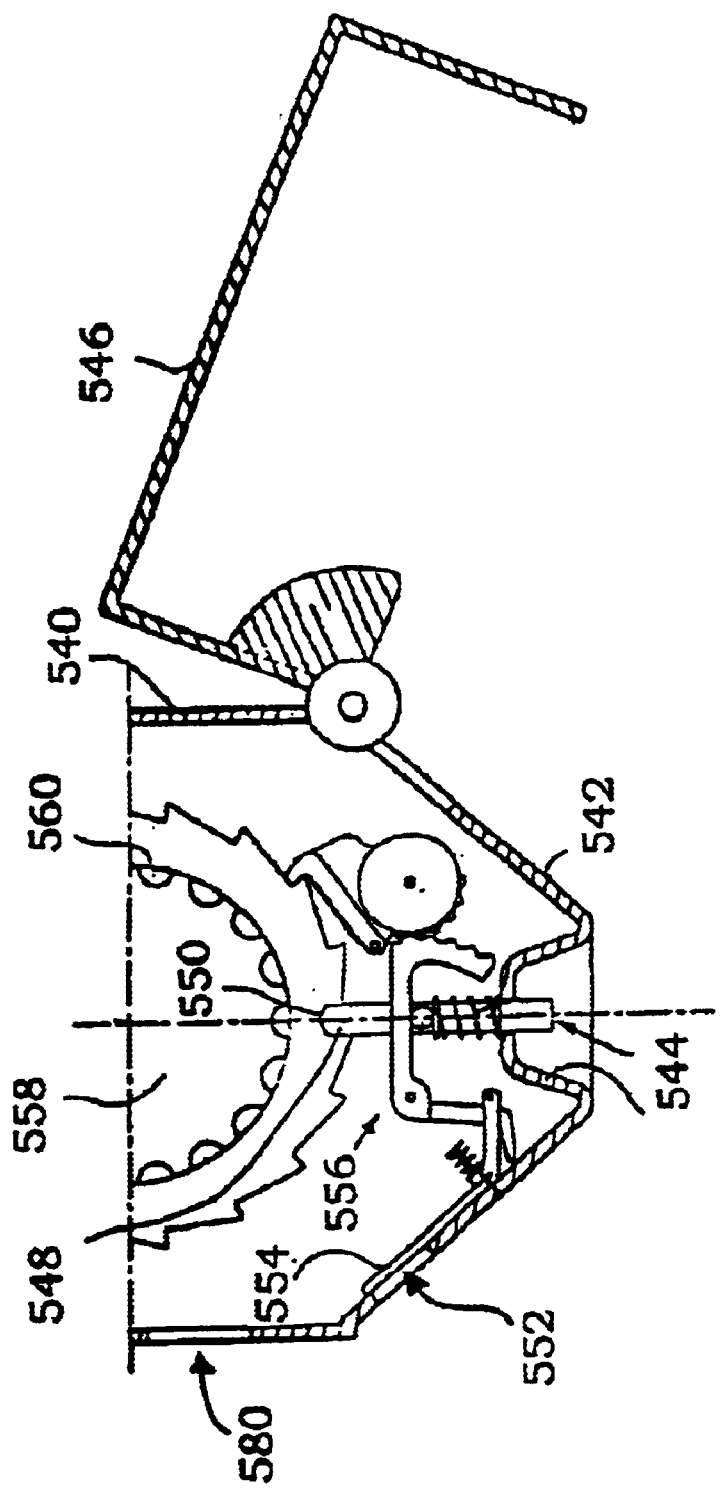
FIG. 29 shows a part view in cross-section of an inhaler for powder medicament with a device according to the fifth feature of the invention.
Figure 30:
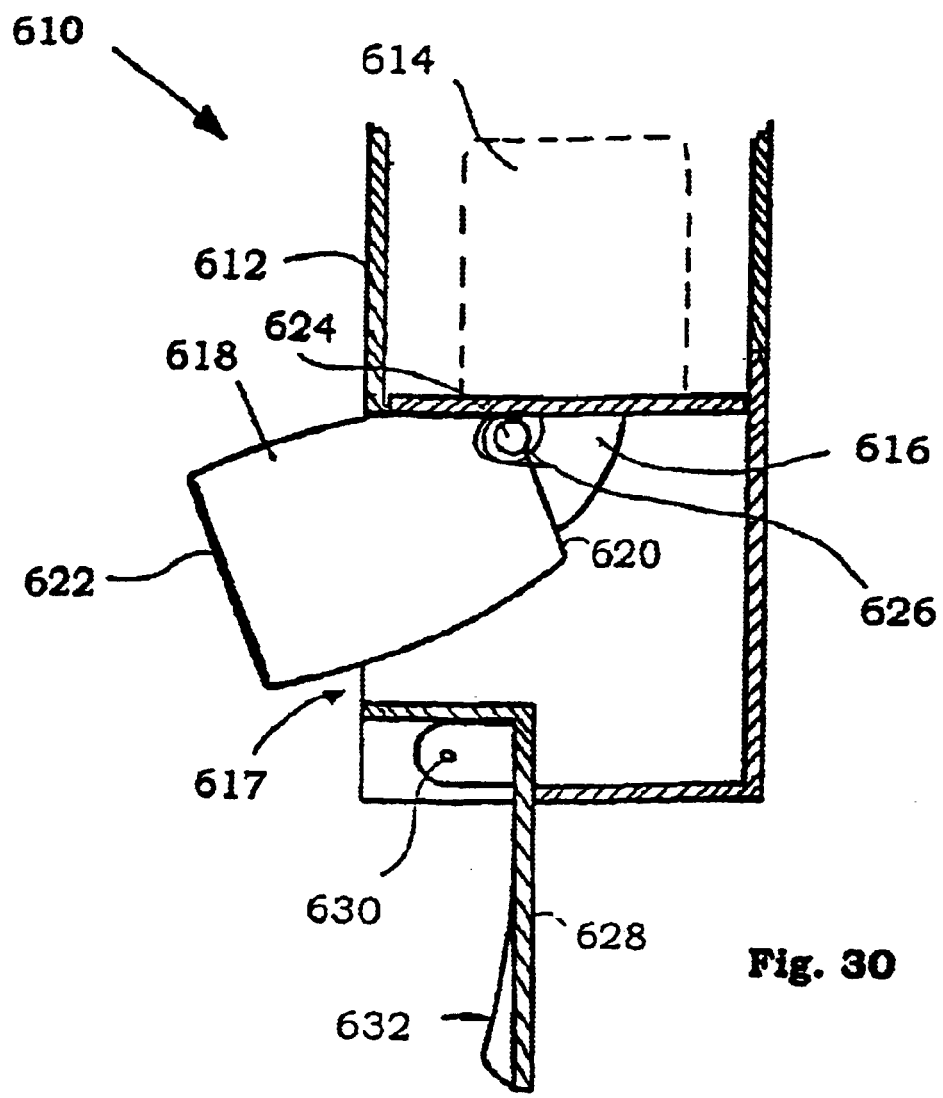
FIG. 30 is a detailed view of a part of an inhaler in cross-section with a first embodiment of a sixth feature of the invention.
Figure 31:
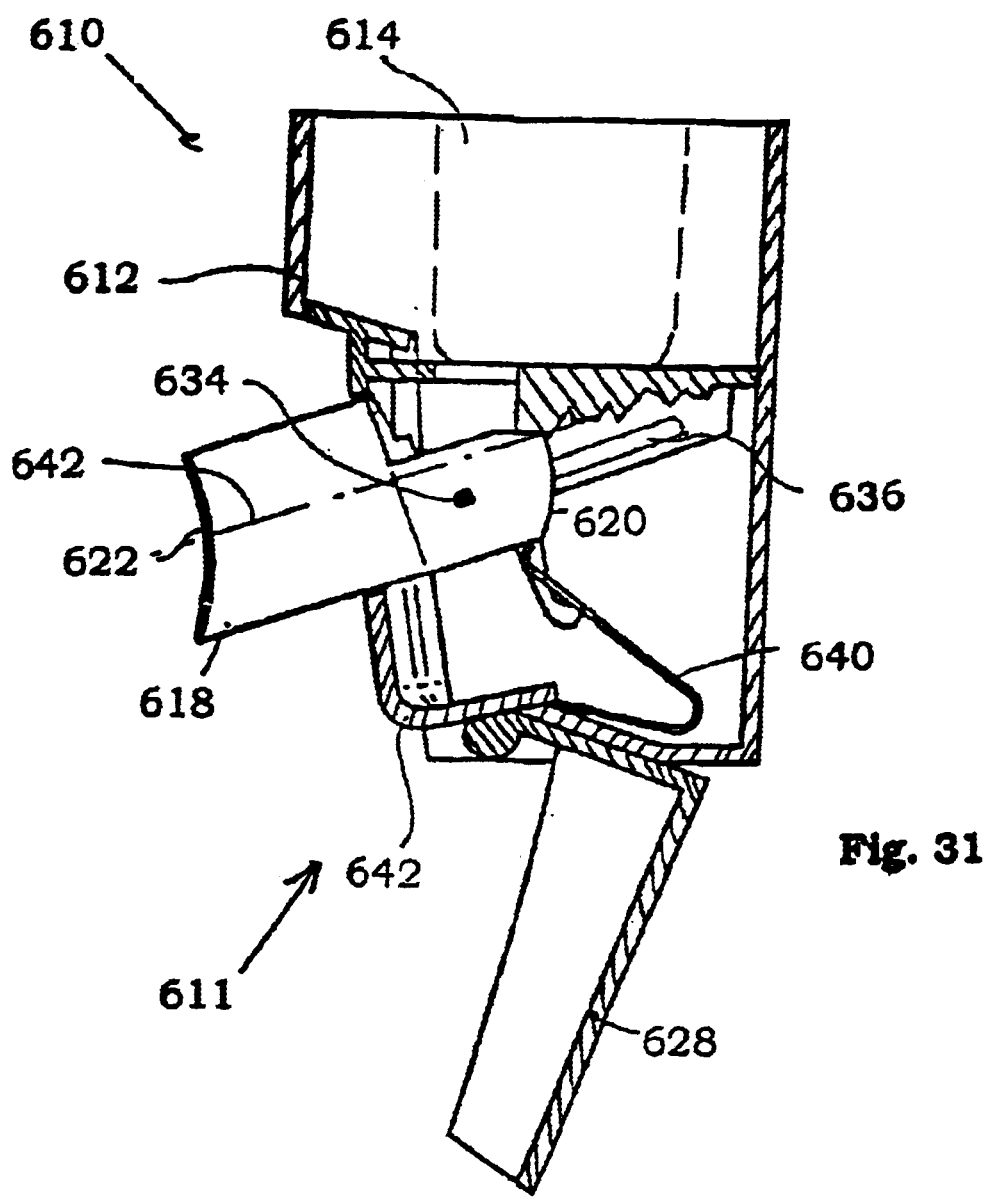
FIG. 31 is a detailed view of a part of an inhaler in cross-section with a second embodiment of the sixth feature of the invention.
Figure 38:
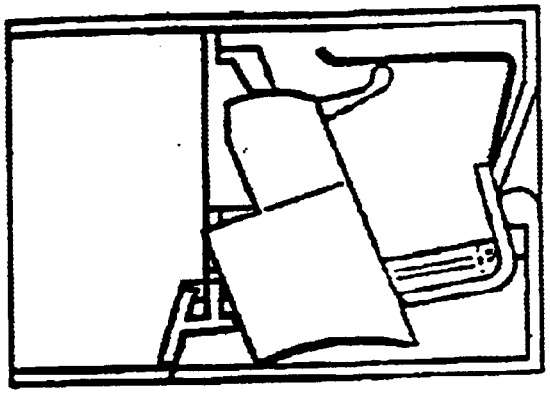
FIGS. 36-38 shows the function of the second embodiment.
Figure 37:
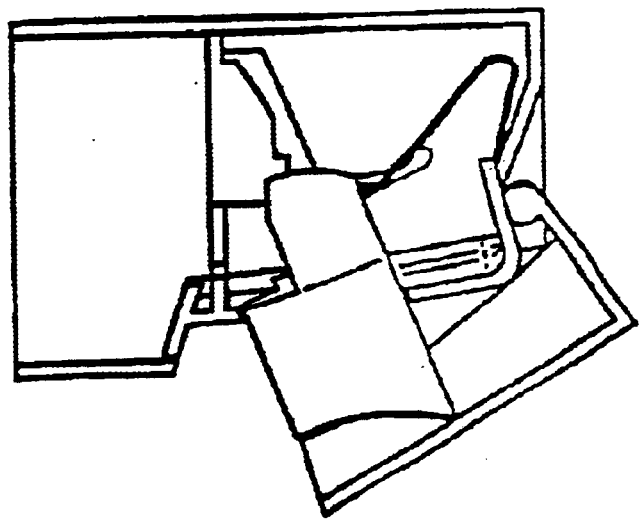
Figure 36:
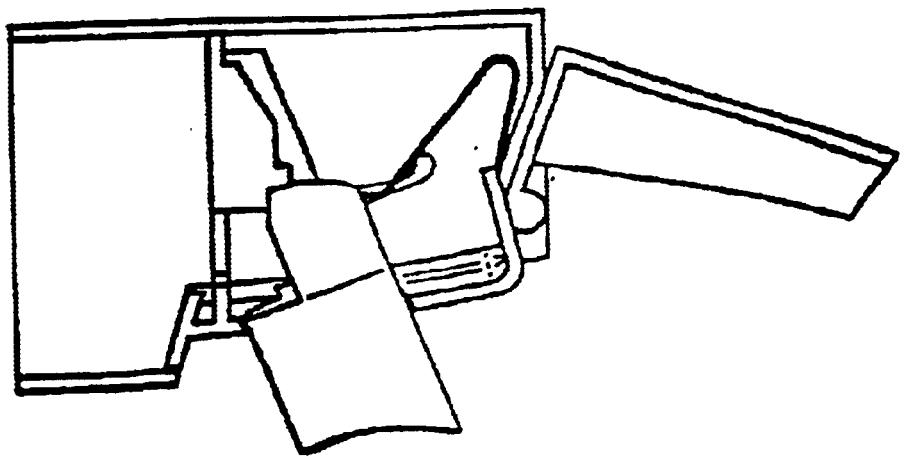

FIG. 29 shows another example of an inhaler where the present invention is utilised. The inhaler shown is intended for medicament in powder form. The inhaler comprises a housing 540. At one end of the housing a mouthpiece 542 with an inhalation opening 544 is arranged. The mouthpiece can be protected by a protective cover 546.

Arranged inside the opening is a means for enabling access to medicament. The means comprises an elongated body 548 with a passage through its length, hereafter named outlet passage. One end 550, the one facing inwards, is arranged with sharpened edges. The elongated body is slidably supported in a hole in the opening, whereby the other end of the elongated body is arranged in the opening. An activating means is arranged to the elongated body, comprising an air intake 552, a flap 554 pivotally arranged adjacent the air intake and a mechanism 556 designed to be able of moving the elongated body inwards when the flap is opened.

Further inside the inhaler and the elongated body a wheel 558 is rotatably arranged. The wheel is arranged with a plurality of recesses 560 and means for rotating the wheel to different positions.

The medicament is packaged in blisters, where each blister enclosure contains one dose of medicament. The blister enclosures are placed in the recesses.

The inhaler further comprises a safety means. It comprises at least one auxiliary air intake 580 arranged to communicate with the inhaler interior, forming an auxiliary air passage with the inhalation opening.

During normal use, without the device according to the invention, the inhalation causes a pressure difference between the interior and the exterior of the inhaler. This pressure difference causes the flap 554 to open and an air flow to be created through the air intake 552 and the passage of the elongated body 548. The movement of the flap causes the activating means to move the elongated body forward so that its pointed end penetrates the blister enclosure whereby a passage between the interior of the enclosure and the inhalation opening is created so that medicament is inhaled.

When the safety device according to the invention is used with the inhaler and the auxiliary air intake 580 is closed, the function is as described above.

If on the other hand someone tries to inhale without closing the auxiliary air intake, an air flow passage is created from the auxiliary air intake 580 through passage of the elongated body to the inhalation opening, thereby preventing a build-up of a pressure difference inside the inhaler. Because no pressure difference is created, the flap will not be affected by the inhalation.

In this context it is to be understood that the auxiliary air intake may be closed or blocked by the fingers of the patient or by a mechanical means. Since the greatest risk of unintentional inhalation is from children, the air intakes should preferably be placed so that a child cannot close the auxiliary intake without great effort.

There are several ways of obtaining this. One way is that the size of the auxiliary air intake is such that a child's ringer cannot block it. Another way is that there are several auxiliary air intakes arranged in the inhaler housing so that it is difficult for a child to place several fingers over all of the intakes. Further the distance between the intakes could be such that it is impossible for a child's hand to reach all the intakes.

If the medicament is of a very potent, toxic, or even lethal kind, if inhaled wrongly, the device could be designed such, and with the auxiliary air intakes positioned such that both hands are needed in order to cover or block all intakes.

In this context it is to be noted that, if more than one auxiliary air intake is used, the activating means is arranged such that it is only activated when a pressure drop corresponding to a complete blocking of all intakes is reached, i e it shall not be sufficient to block some of the auxiliary air intakes in order to activate the inhaler. By providing different number of openings and by arranging these with different configurations, different "levels of security" may be obtained with the present invention.

A sixth feature of the present invention will now be described in connection with FIGS. 30–40. An inhaler 610 comprising a device 611 according to the invention consists of a body 612, where only the lower part is shown in the drawings, a compartment 614 containing medicament, an air passage 616 and an opening 617. The compartment is in a known way connected to the air passage 616 for dispensing of a metered dose of medicament to the patient during inhalation.

The device according to the invention comprises a mouthpiece 18 with a back and a front end 620, 622 in fluid communication with the air passage. In the embodiment shown in FIGS. 30 and 32–35, the back end 620 is pivotably arranged to an axis 624 inside the body so that the mouthpiece may be pivoted between a rest/protected position, FIG. 35, to an activated, ready-to-use position, FIGS. 30 and 32. A torsion spring 626 is arranged between the mouthpiece and the body for urging the mouthpiece towards the activated position and for holding it in that position.

A protective cover or lid 628 is pivotably arranged to an axis 630. The inside of the cover is arranged with a protruding surface 632. When the inhaler/mouthpiece is activated and ready to use, the mouthpiece has swung to its protruding, inhalation, position by the torsion spring, whereby the upper side surface of the mouthpiece abuts the upper edge of the opening 617 pushed by the spring.

When the patient has inhaled the dose of medicament, he closes the cover by pivoting it. The inner surface of the cover then comes in contact with the front end of the mouthpiece, which surface pivots the mouthpiece into the body, FIGS. 33 and 34. When the cover is completely shut, it is held in place by a fixating means (not shown) thereby holding the mouthpiece in the rest/protected position.

FIGS. 31 and 36–38 show another embodiment of the invention, where the same components have the same reference numerals.

In this embodiment the mouthpiece is arranged slidable in the body. The mouthpiece is arranged with protrusions 634 attached to opposite side of the mouthpiece. The protrusions are slidably arranged in grooves 636 in the body. The inner end of the mouthpiece is arranged with a downward extending arm 638. A pusher spring 640 is arranged between the mouthpiece and the body. An enclosing wall 642 is arranged around the mouthpiece. With this design the whole interior of the body may act as an air passage for the inhaling air, and thus no specific air passage is to be arranged and connected to the mouthpiece. The wall also serves as a guide and support for the mouthpiece.

When the inhaler is activated, the mouthpiece protrudes through the opening by the spring and held in this position, while the protrusions abut the outer ends of the grooves. When the patient has inhaled the dose of medicament, he closes the cover by pivoting it. The inner surface of the cover then pushes the mouthpiece whereby it slides in its longitudinal direction 642 by the protrusions and the groove.

FIG. 39 shows an example of an inhaler for aerosol driven medicaments with a pivoting mouthpiece. The pivoting point 650 is placed such that the nozzle 652 in fluid communication with the canister 654 is in line with the mouthpiece 618 when it is in the inhaling position. A general desire in this respect is that the pivoting point is placed as close to the canister/nozzle as possible to minimise the height of the inhaler, and as far to the protruding side of the inhaler/mouthpiece as possible so that the mouthpiece protrudes such an extent that it is easily placed in the mouth. The pivoting mouthpiece is also provided with a covering wall 656, which, when the mouthpiece is in the inhaling position, covers the interior of the inhaler, which may comprise other mechanisms for handling the inhaler. The protective cover/lid may also be arranged with holding means, not shown, for preventing the mouthpiece to pivot back when in the inhaling position.

Figure 40:
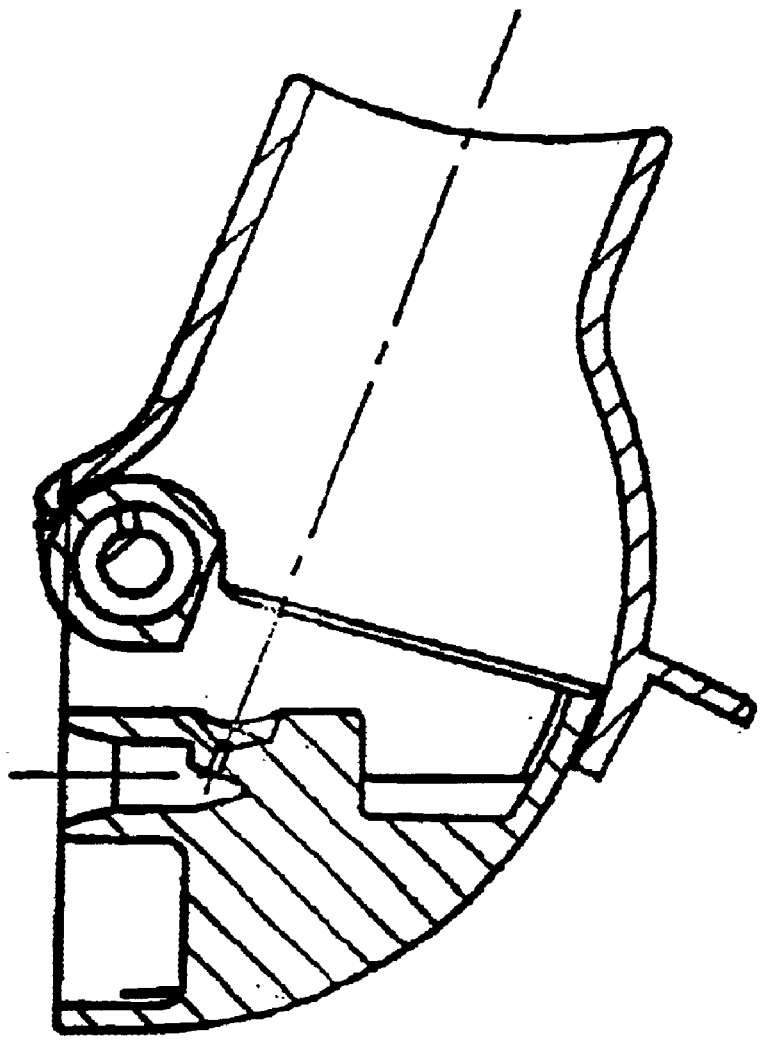
FIG. 40 shows a example of a mouthpiece according to the invention and a spray head as a unit.

FIG. 40 shows a mouthpiece according to the invention wherein the movable mouthpiece and the spray head with nozzle is made as one replaceable unit. This arrangement is convenient when the inhaler as such is intended for long time use. The mouthpiece and the spray head often become clogged or smeared with medicament after some use. Therefore, it is practical that they may be removed as a unit for replacement or cleaning.

For the different embodiments, the protective cover/lid may be opened by pressing or sliding a button, lever or the like, and placed on the inhaler in such a way as to coincide with the ergonomical conditions of the user. In order to ensure that the cover is not opened accidentally, it may comprise two buttons or activating points that have to pressed or activated at the same time. It is also conceivable that the protective cover is a sleeve, for example slidable in the longitudinal direction of the inhaler. The sleeve may also be SD long that it constitutes the major outer surface of the inhaler, and that the user holds the sleeve when holding the inhaler. The upper part of the sleeve is open, through which the inhaler body protrudes. By pressing the upper end of the body downwards, it slides inside the sleeve, whereby the lower part of the body, comprising the movable mouthpiece, is arranged below the sleeve, thus exposing the mouthpiece, and the inhaler is ready to use.

The device can further be provided with means for reactivating, returning and recharging means of the inhaler after delivery of a dose. These means may include placing the inhaler in a ready-to-use state, wherein the metered dose compartment is refilled/recharged, that the means for delivering a dose, like pressure springs acting on an aerosol canister, are re-tensioned, and the like. In this context, reference is made to the Swedish patent application No. 9902349-1, which hereby is incorporated in its entirety. Preferably these means are activated by the protective cover/lid when it is closed. Tensioning of springs and the like is facilitated in that the protective cover/lid may be used as a lever, thereby reducing the force needed.

It is to be understood that the invention is not limited to the embodiments described above and shown on the drawings, but may be altered within the scope of the patent claims.

In this respect it is conceivable that the mouthpiece may be pivotable around a vertically arranged axis instead of a horizontal axis, which axis may coincide with the outlet of the metered dose compartment. This design has the advantage of requiring less space in that the mouthpiece is swung sideways in and out from the inhaler body, thus reducing the height of the inhaler. It is also conceivable that the mouthpiece may be formed by several telescopically acting parts in order to obtain the protruding effect.

The moving action of the mouthpiece from an activated position to a protected rest position may also be obtained by other means, such as cam-shaped ribs or protrusions or some form of linkage between the cover and the mouthpiece.

What is claimed is:

1. Device for use with an inhaler, the inhaler comprising a body, an aerosol canister arranged in said body containing medicament, comprising a metered dose chamber and able to dispense a metered dose of said medicament, a nozzle in fluid communication with said canister, an opening for dispensing of said medicament in fluid communication with said nozzle, said device comprising:

an activator (34,36,42,44,46,50,52) for activating said canister to open and dispense said medicament in response to an airflow in the inhaler caused by inhalation of a user through said opening, and a return controller (42,46,56,58,60) for deactivating said canister to close said opening, wherein, said return controller deactivates said canister when the airflow drops below a certain threshold value, further comprising a drug delivery opening (220), compartment (212) containing medicament to be delivered, an energy system comprising actuating means (244, 274) capable of delivering a dose of medicament from the compartment and activating means (222,226,230, 236) capable of activating said actuating means, whereupon activation of the device a force/energy acting on the activating means is transmitted to the actuating means, whereby a dose of medicament is delivered through said drug delivery opening, characterized in that said energy system is divided in at least a first and a second energy system, the first energy system comprising said activating (222,226) means and a release means (230,236), said second energy system comprising said actuating means (244,274) and a locking means (250,260,264,268) operatively connected to the actuating means and capable of locking said actuating means in an energized state, wherein the systems, when the device is non-activated, are in no physical contact with each other, and wherein, upon activation of the activating means, the release means is moved into contact with, and moves, the locking means out of a locking position.

2. Device according to claim 1, characterized in that the activating means and release means are designed and adapted such that the force/energy provided by the first energy system upon activation is substantially higher than the force/energy required for releasing the second energy system.

3. Device according to claim 1, characterized in that the second energy system comprises a transmission, by which the force/energy required for releasing said locking means is substantially less than the force/energy required for holding said actuating means in an energized state.

4. Device according to claim 1, characterized in that the force/energy available from said first energy system is adapted such that it is substantially above the variations in force/energy requirements for activating the second energy system.

5. Device according to claim 1, characterized in that said first energy system is calibrated such that the activating means is activated at a predetermined threshold.

6. Device according to claim 1, characterized in that it is arranged in an inhaler, and that the activating means is arranged and adapted such that it is activated upon inhalation.

7. Device according to claim 1, characterized in that the activating means comprises a flap or vane arranged in said inhaler adjacent an air intake of said inhaler.

8. Device according to claim 1, characterized in that the device is arranged in a medical injection device, and is arranged and adapted such that the activating means comprises a user-operated means, whereby, upon operation, the release means moves the locking means out of a locking position.

9. Medical distributor for distributing medicament to a patient comprising plural devices according to claim 1, characterized in that the medical distributor comprises plural devices acting in sequence of each other, dependent or independent of each other.

10. Medical distributor according to claim 9, characterized in that the activating means of one device is activated upon start of inhalation and in that the activating means of a second device is activated upon termination of inhalation.

11. Inhaler comprising the device according to claim 1.

12. Medical injector comprising the device according to claim 1.

* * * * *